United States Patent
Esperet et al.

(10) Patent No.: US 11,136,388 B2
(45) Date of Patent: Oct. 5, 2021

(54) BIOMARKERS FOR ANTI-IL4-IL13 BISPECIFIC ANTIBODIES

(71) Applicant: Sanofi, Paris (FR)

(72) Inventors: Corinne Esperet, Paris (FR); Alexandre Jagerschmidt, Paris (FR); Christina Soubrane, Paris (FR); Arun Subramaniam, Bridgewater, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/297,419

(22) Filed: Mar. 8, 2019

(65) Prior Publication Data

US 2019/0359703 A1 Nov. 28, 2019

Related U.S. Application Data

(63) Continuation of application No. 15/320,106, filed as application No. PCT/IB2015/001377 on Jun. 26, 2015, now abandoned.

(60) Provisional application No. 62/102,555, filed on Jan. 12, 2015, provisional application No. 62/102,097, filed on Jan. 11, 2015, provisional application No. 62/018,253, filed on Jun. 27, 2014.

(30) Foreign Application Priority Data

Sep. 24, 2014 (EP) .................................. 14306477

(51) Int. Cl.
G01N 33/68 (2006.01)
C07K 16/24 (2006.01)
A61K 39/02 (2006.01)
A61K 39/395 (2006.01)
C07K 14/52 (2006.01)
C07K 16/46 (2006.01)
A61K 39/00 (2006.01)

(52) U.S. Cl.
CPC ............ *C07K 16/247* (2013.01); *A61K 39/02* (2013.01); *A61K 39/395* (2013.01); *C07K 14/521* (2013.01); *C07K 16/244* (2013.01); *C07K 16/468* (2013.01); *G01N 33/6893* (2013.01); *A61K 2039/505* (2013.01); *A61K 2039/54* (2013.01); *A61K 2039/545* (2013.01); *C07K 2317/31* (2013.01); *C07K 2317/33* (2013.01); *C07K 2317/76* (2013.01); *C07K 2317/90* (2013.01); *C07K 2317/92* (2013.01); *C07K 2317/94* (2013.01); *G01N 2333/521* (2013.01); *G01N 2800/52* (2013.01)

(58) Field of Classification Search
CPC .................................................. G01N 33/6893
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,807,715 A | 9/1998 | Morrison et al. | |
| 5,869,619 A | 2/1999 | Studnicka | |
| 5,989,830 A | 11/1999 | Davis et al. | |
| 7,612,181 B2 | 11/2009 | Wu et al. | |
| 8,388,965 B2 | 3/2013 | Rao et al. | |
| 9,732,162 B2 | 8/2017 | Rao et al. | |
| 9,738,728 B2 | 8/2017 | Rao et al. | |
| 2011/0052598 A1 | 3/2011 | Watarai et al. | |
| 2013/0209469 A1 | 8/2013 | Rao et al. | |
| 2013/0236460 A1 | 9/2013 | Rao et al. | |
| 2013/0236461 A1 | 9/2013 | Rao et al. | |
| 2013/0236462 A1 | 9/2013 | Rao et al. | |
| 2013/0236463 A1 | 9/2013 | Rao et al. | |
| 2013/0243776 A1 | 9/2013 | Rao et al. | |
| 2013/0243778 A1 | 9/2013 | Rao et al. | |
| 2013/0251717 A1 | 9/2013 | Rao et al. | |
| 2013/0251718 A1 | 9/2013 | Rao et al. | |
| 2013/0259866 A1 | 10/2013 | Rao et al. | |
| 2013/0344074 A1 | 12/2013 | Bender et al. | |
| 2014/0023649 A1 | 1/2014 | Rao et al. | |
| 2014/0072583 A1 | 3/2014 | Ardeleanu et al. | |
| 2015/0225479 A1 | 8/2015 | Huille et al. | |
| 2016/0075777 A1 | 3/2016 | Carayon et al. | |
| 2017/0029498 A1 | 2/2017 | Bender et al. | |
| 2017/0145089 A1 | 5/2017 | Esperet et al. | |
| 2018/0030156 A1 | 2/2018 | Rao et al. | |

FOREIGN PATENT DOCUMENTS

| | | |
|---|---|---|
| EP | 0 239 400 A2 | 9/1987 |
| EP | 0 332 424 A2 | 9/1989 |
| EP | 0 338 745 A1 | 10/1989 |
| JP | 2008520684 A | 6/2008 |

(Continued)

OTHER PUBLICATIONS

Shinoda et al (2009), Respiration, 78:285-292.*
Rudikoff et al. Proc. Natl. Acad. Sci. USA vol. 79, pp. 1979-1983 (Mar. 1982).*
Janeway et al. Immunology, 3rd ed., 1997, Garland Publications, Inc., pp. 3:1-3:11.*
Altschul, S.F. et al. (Oct. 5, 1990). "Basic Local Alignment Search Tool," *Journal Mol. Biol.* 215(3):403-410.

(Continued)

*Primary Examiner* — Prema M Mertz
(74) *Attorney, Agent, or Firm* — Morrison & Foerster LLP

(57) ABSTRACT

Disclosed herein are safe doses of dual-V-region antibody-like binding proteins or fragments thereof, as well as methods for assessing binding of dual-V-region antibody-like proteins or fragments thereof to their targets, and methods of treating idiopathic pulmonary fibrosis (IPF) by administering safe doses of dual-V-region antibody-like binding proteins or fragments thereof. In some embodiments, the dual-V-region antibody-like binding proteins or fragments thereof bind both IL-4 and IL-13.

6 Claims, 19 Drawing Sheets

Specification includes a Sequence Listing.

(56) References Cited

FOREIGN PATENT DOCUMENTS

| | | |
|---|---|---|
| JP | 2011-501671 A | 1/2011 |
| JP | 2014506321 A | 3/2014 |
| JP | 2014-510730 A | 5/2014 |
| WO | WO-1989/09622 A1 | 10/1989 |
| WO | WO-1993/21319 A1 | 10/1993 |
| WO | WO-2003/035847 A2 | 5/2003 |
| WO | WO-2003/038041 A2 | 5/2003 |
| WO | WO-2006/042333 A2 | 4/2006 |
| WO | WO-2009/052081 A2 | 4/2009 |
| WO | WO-2011/052598 A1 | 3/2011 |
| WO | WO-2012/125775 A1 | 9/2012 |
| WO | WO-2014/031610 A1 | 2/2014 |
| WO | WO-2014/177568 A1 | 11/2014 |
| WO | WO-2015/121318 A1 | 8/2015 |

OTHER PUBLICATIONS

Aversa, G. et al. (Dec. 1, 1993). "An Interleukin 4 (IL-4) Mutant Protein Inhibits Both IL-4 or IL-13—Induced Human Immunoglobulin G4 (IgG4) and IgE Synthesis and B Cell Proliferation: Support for a Common Component Shared by IL-4 and IL-13 Receptors," *J. Exp. Med.* 178(6):2213-2218.

Carter, P. (Feb. 1, 2001). "Bispecific Human IgG by Design," *J. Immunol. Methods* 248(1-2):7-15.

Carter, P. et al. (1995). "Toward the Production of Bispecific Antibody Fragments for Clinical Applications," *Journal of Hematotherapy* 4(5):463-470.

Carter, P. et al. (May 15, 1992). "Humanization of an Anti-p185$^{HER2}$ Antibody for Human Cancer Therapy," *Proc Natl Acad Sci USA* 89(10):4285-4289.

Chothia, C. et al. (Aug. 20, 1987). "Canonical Structures for the Hypervariable Regions of Immunoglobulins," *J Mol Biol* 196(4):901-917.

De Waal Malefyt, R. et al. (Dec. 1, 1993). "Effects of IL-13 on Phenotype, Cytokine Production, and Cytotoxic Function of Human Monocytes. Comparison with IL-4 and Modulation by IFN-γ or IL-10," *The Journal of Immunology* 151(11):6370-6381.

Defrance, T. et al. (Jan. 1, 1994). "Interleukin 13 is a B Cell Stimulating Factor," *J. Exp. Med.* 179(1):135-143.

Derocq, J.-M. et al. (Apr. 18, 1994). "Interleukin-13 Stimulates Interleukin-6 Production by Human Keratinocytes: Similarity with Interleukin-4," *FEBS Lett.* 343(1):32-36.

Doyle, A.G. et al. (Jun. 1994). "Interleukin-13 Alters the Activation State of Murine Macrophages In Vitro: Comparison with Interleukin-4 and Interferon-γ," *European Journal of Immunology* 24(6):1441-1445.

Eferl, R. et al. (Jul. 29, 2008). "Development of Pulmonary Fibrosis Through a Pathway Involving the Transcription Factor Fra-2/AP-1," *Proc. Natl. Acad. Sci.* 105(30):10525-10530.

Fior, R. et al. (Nov.-Dec. 1994). "Interleukin-13 Gene Expression by Malignant and EBV-Transformed Human B Lymphocytes," *European Cytokine Network* 5(6):593-600.

Faffe, D.S. et al. (Oct. 2003). "IL-13 and IL-4 Promote TARC Release in Human Airway Smooth Muscle Cells: Role of IL-4 Receptor Genotype," *Am J Physiol Lung Cell Mol Physiol.* 285(4):L907-L914.

Gillies, S.D. et al. (Dec. 20, 1989). "High-Level Expression of Chimeric Antibodies Using Adapted cDNA Variable Region Cassettes," *Journal of Immunological Methods* 125(1-2):191-202.

Gordon, S. et al. (May 28, 2010). "Alternative Activation of Macrophages: Mechanism and Functions," *Immunity* 32(5):593-604.

Heinzmann, A. el al. (Mar. 1, 2000). "Genetic Variants of IL-13 Signalling and Human Asthma and Atopy," *Human Molecular Genetics* 9(4):549-559.

Herbert, J.M. et al. (Aug. 16, 1993). "IL-4 and IL-13 Exhibit Comparable Abilities to Reduce Pyrogen-Induced Expression of Procoagulant Activity in Endothelial Cells and Monocytes," *FEBS Lett.* 328(3):268-270.

Hudson, P.J. (Oct. 1999). "Recombinant Antibody Constructs in Cancer Therapy," *Curr Opin Immunol.* 11(5):548-557.

Jakubzick, C. et al. (Jun. 2004). "Human Pulmonary Fibroblasts Exhibit Altered Interleukin-4 and Interleukin-13 Receptor Subunit Expression in Idiopathic Interstitial Pneumonia," *American Journal of Pathology* 164(6):1989-2001.

Janeway, C.A Jr. et al. (1997). "Structure of the Antibody Molecule and Immunoglobulin Genes," Chapter 3 in *ImmunoBiology—The Immune System in Health and Disease*, Penelope Austin (ed.) et al.; 3$^{rd}$ Edition, Current Biology/Ltd./Garland Publishing Inc.,NY, fourteen pages.

Kakinuma, T. et al. (Oct. 7, 2002). "IL-4, but not IL-13, modulates TARC (Thymus and Activation-Regulated Chemokine)/CCL17 and IP-10 (Interferon-Induced Protein of 10kDA)/CXCL10 Release by TNF-Alpha and IFN-Gamma in HaCat Cell Line," *Cytokine* 20(1):1-6.

Köhler, G. et al. (Aug. 7, 1975). "Continuous Cultures of Fused Cells Secreting Antibody of Predefined Specificity," *Nature* 256(5517):495-497.

Lazar, G.A. et al. (Mar. 2007; e-published on Oct. 31, 2006). "A Molecular Immunology Approach to Antibody Humanization and Functional Optimization," *Molecular Immunology* 44(8):1986-1998.

Lefort, S. et al. (Jun. 12, 1995). "IL-13 and IL-4 Share Signal Transduction Elements as well as Receptor Components in TF-1 Cells," *FEBS Lett.* 366(2-3):122-126.

Liddiard, K. et al. (Nov. 29, 2006). "Interleukin-4 Induction of the CC Chemokine TARC (CCL17) in Murine Macrophages is Mediated by Multiple STAT6 Sites in the TARC Gene Promoter," *BMC Molecular Biology* 7:45, pp. 1-18.

McKenzie, A.N. et al. (Apr. 15, 1993). "Interleukin 13, a T-cell-derived Cytokine That Regulates Human Monocyte and B-Cell Function," *Proc. Natl. Acad. Sci. U.S.A* 90(8):3735-3739.

Miller, K. et al. (May 1, 2003). "Design, Construction, and In Vitro Analyses of Multivalent Antibodies," *The Journal of Immunology* 170(9):4854-4861.

Milstein, C. et al. (Oct. 6, 1983). "Hybrid Hybridomas and their Use in Immunohistochemistry," *Nature* 305:537-540.

Minty, A. et al. (Mar. 18, 1993). "Interleukin-13 is a New Human Lymphokine Regulating Inflammatory and Immune Responses," *Nature* 362(6417):248-250.

Monick, M.M. et al. (Aug. 1, 2007). "Respiratory Syncytial Virus Synergizes with Th2 Cytokines to Induce Optimal Levels of TARC/CCL17," *The Journal of Immunology* 179(3):1648-1658.

Montaner, L.J. et al. (Aug. 1, 1993). "Interleukin 13 Inhibits Human Immunodeficiency Virus Type 1 Production in Primary Blood-Derived Human Macrophages In Vitro," *The Journal of Experimental Medicine* 178(2):743-747.

Morello, D. et al. (Aug. 1986). "Studies on the Expression of an H-2K/Human Growth Hormone Fusion Gene in Giant Transgenic Mice," *The EMBO Journal* 5(8):1877-1883.

Morrison et al. (Nov. 1984). "Chimeric Human Antibody Molecules: Mouse Antigen-Binding Domains With Human Constant Region Domains," *Proc Natl Acad Sci USA* 81(21):6851-6855.

Morrison, S.L. (Sep. 20, 1985). "Transfectomas Provide Novel Chimeric Antibodies," *Science* 229(4719):1202-1207.

Murata, T. et al. (Jan. 1999). "Sharing of Receptor Subunits and Signal Transduction Pathway Between the IL-4 and IL-13 Receptor System," *Int. J. Hematol.* 69(1):13-20.

Murray, L.A. et al. (2008; e-published on Feb. 23, 2008). "Hyper-Responsiveness of IPF/UIP Fibroblasts: Interplay Between TGFβ1, IL-13 and CCL2," *The International Journal of Biochemistry & Cell Biology* 40(10):2174-2182.

Muzio, M.R.F. et al. (Apr. 1, 1994). "Interleukin-13 Induces the Production of Interleukin-1 Receptor Antagonist (IL-1ra) and the Expression of the mRNA for the Intracellular (keratinocyte) Form of IL-1ra in Human Myelomonocytic Cells," *Blood* 83(7):1738-1743.

Ngoc, L.P. et al. (Apr. 2005). "Cytokines, Allergy, and Asthma," *Current Opinion in Allergy & Clinical Immunology* 5(2):161-166.

Oi, V.T. et al. (1986). "Chimeric Antibodies," *BioTechniques* 4(3):214-221.

(56) References Cited

OTHER PUBLICATIONS

Pearson, W.R. et al. (Apr. 1988). "Improved Tools for Biological Sequence Comparison," *Proc Natl Acad Sci USA* 85(8):2444-2448.
Plückthun, A. et al. (1997). "New Protein Engineering Approaches to Multivalent and Bispecific Antibody Fragments," *Immunotechnology* 3:83-105.
Presta, L.G. et al. (Sep. 1, 1993). "Humanization of an Antibody Directed Against IgE," *J Immunol.* 151(5):2623-2632.
Punnonen, J. et al. (Apr. 15, 1993). "Interleukin 13 Induces Interleukin 4-Independent IgG4 and IgE Synthesis and CD23 Expression by Human B Cells," *Proc. Natl. Acad. Sci. (USA)* 90(8):3730-3734.
Ritter, M. et al. (Aug. 19, 2005; e-published on Jun. 27, 2005). "Elevated Expression of TARC (CCL17) and MDC (CCL22) in Models of Cigarette Smoke-Induced Pulmonary Inflammation," *Biochemical and Biophysical Research Communications* 334(1):254-262.
Rudikoff, S. et al. (Mar. 1982). "Single Amino Acid Substitution Altering Antigen-Binding Specificity," *Proc. Natl. Acad. Sci. U.S.A.* 79:1979-1983.
Sims, M.J. et al. (Aug. 15, 1993). "A Humanized CD18 Antibody Can Block Function Without Cell Destruction," *The Journal of Immunology* 151(4):2296-2308.
Sozzani, P. et al. (Mar. 10, 1995). "Interleukin-13 Inhibits Protein Kinase C-triggered Respiratory Burst in Human Monocytes," *The Journal of Biological Chemistry* 270(10):5084-5088.
Staerz, U.D. et al. (Apr. 18, 1985). "Hybrid Antibodies Can Target Sites for Attack by T cells," *Nature* 314:628-631.
Studnicka, G.M. et al. (Jun. 1994). "Human-engineered Monoclonal Antibodies Retain Full Specific Binding Activity by Preserving Non-CDR Complementarity-Modulating Residues," *Protein Engineering* 7(6)805-814.
Tanaka, T. et al. (1996). "Interleukin-6" Chapter 10 in *Cytokine Regulation of Humeral Immunity: Basic and Clinical Aspects*, Snapper, M.C. (ed.), John Wiley and Sons, New York, pp. 251-272, twenty two pages.
Todorovska, A. et al. (Feb. 1, 2001). "Design and Application of Diabodies, Triabodies and Tetrabodies for Cancer Targeting," *Journal of Immunological Methods* 248(1-2):47-66.
Vita, N. et al. (Feb. 24, 1995). "Characterization and Comparison of the Interleukin 13 Receptor with the Interleukin 4 Receptor on Several Cell Types," *The Journal of Biological Chemistry* 270(8):3512-3517.
Winter, G. et al. (Jan. 24, 1991). "Man-made Antibodies," *Nature* 349(6307):293-299.
Wirnsberger, G. et al. (Jul. 2006). "IL-4 Induces Expression of TARC/CCL17 via Two STAT6 Binding Sites," *Eur J Immunol.* 36(7):1882-1891.
Wynn, T.A. (Aug. 2004). "Fibrotic Disease and the $T_H1/T_H2$ Paradigm," *Nat. Rev. Immunol*, 4(8):583-594.
Zurawski, G. et al. (Jan. 1994). "Interleukin 13, an Interleukin 4-Like Cytokine that Acts on Monocytes and B Cells, but not on T Cells," *Immunol. Today* 15(1):19-26.
Zurawski, S. M. et al. (Jul. 1993). "Receptors for Interleukin-13 and Interleukin-4 are Complex and Share a Novel Component that Functions in Signal Transduction," *The EMBO Journal* 12(7):2663-2670.
International Preliminary Report on Patentability dated Dec. 27, 2016 for PCT Application No. PCT/IB2015/001377 filed on Jun. 26, 2015, eleven pages.
International Search Report dated Feb. 3, 2016 for PCT Application No. PCT/IB2015/001377 filed on Jun. 26, 2015, eight pages.
Written Opinion of the International Searching Authority dated Feb. 3, 2016, for PCT Application No. PCT/IB2015/001377 filed on Jun. 26, 2015, ten pages.
Agrawal, S. et al. (2014, e-pub Nov. 28, 2013). "Role of Periostin, FENO, IL-13, Lebrikzumab, Other IL-13 Antagonists and Dual IL-4/IL-13 Antagonist in Asthma," Expert Opinion on Biological Therapy 14(2)165-181.
Swanson, B. (Feb. 3, 2014). "Poster 1023: Dupilumab Suppresses Th2 Inflammation in Adult Asthma and Atopic Dermatitis," World Allergy Organization Journal 7(1):P13, 2 pages.
Swanson, B.N. et al. (Feb. 2014). "Exhaled Nitric Oxide (FeNO) and T-Helper 2 Cell Biomarkers: Can They Predict Treatment Response to Dupilumab, An IL-4R alpha Antibody, In an Eosinophilic Asthma Population?" Journal of Allergy and Clinical Immunology 133(2):AB85, Abstract No. 297, 2 pages.
Wenzel, S. et al. (Jun. 27, 2013). "Dupilumab in Persistent Asthma With Elevated Eosinophil Levels," New England Journal of Medicine 368(26):2455-2466.
Oh, C.K. et al. (Mar. 1, 2010). "Investigational Therapeutics Targeting The IL-4/IL-13/STAT-6 Pathway For The Treatment Of Asthma", European Respiratory Review 19(115):46-54.

\* cited by examiner

SEQUENCE LISTING

```
<160> NUMBER OF SEQ ID NOS: 7

<210> SEQ ID NO 1
<211> LENGTH: 111
<212> TYPE: PRT
<213> ORGANISM: Artificial Sequence
<220> FEATURE:
<223> OTHER INFORMATION: humanized mouse/ mouse VL3 region

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: humanized mouse/mouse VH2 region

<400> SEQUENCE: 2

Glu Val Gln Leu Lys Glu Ser Gly Pro Gly Leu Val Ala Pro Gly Gly
1               5                   10                  15
```

```
Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser
        115

<210> SEQ ID NO 3
<211> LENGTH: 108
<212> TYPE: PRT
<213> ORGANISM: Artificial Sequence
<220> FEATURE:
<223> OTHER INFORMATION: humanized mouse/mouse VL1 region

<400> SEQUENCE: 3

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg
            100                 105

<210> SEQ ID NO 4
<211> LENGTH: 124
<212> TYPE: PRT
<213> ORGANISM: Artificial Sequence
<220> FEATURE:
<223> OTHER INFORMATION: humanized mouse/mouse VH1 region

<400> SEQUENCE: 4

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95
```

```
Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 5
<211> LENGTH: 124
<212> TYPE: PRT
<213> ORGANISM: Artificial Sequence
<220> FEATURE:
<223> OTHER INFORMATION: humanized mouse/mouse VH2 region

<400> SEQUENCE: 5

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Ala Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 6
<211> LENGTH: 10
<212> TYPE: PRT
<213> ORGANISM: Artificial Sequence
<220> FEATURE:
<223> OTHER INFORMATION: linker

<400> SEQUENCE: 6

Gly Gly Gly Gly Ser Gly Gly Gly Gly Ser
1               5                   10

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ggaggcggag ggtccggagg cggaggatcc                                    30
```

BIOMARKERS FOR ANTI-IL4-IL13 BISPECIFIC ANTIBODIES

CROSS REFERENCE TO RELATED APPLICATIONS

This application is a continuation of U.S. patent application Ser. No. 15/320,106, which adopts the international filing date of Jun. 26, 2015, which is a National Phase application under 35 U.S.C. § 371 of International Application No. PCT/IB2015/001377 filed Jun. 26, 2015, which claims priority benefit of U.S. Provisional Application No. 62/018,253, filed Jun. 27, 2014, U.S. Provisional Application No. 62/102,097, filed Jan. 11, 2015, U.S. Provisional Application No. 62/102,555, filed Jan. 12, 2015, and EP Application No. 14306477.2 filed Sep. 24, 2014, the disclosures of each of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952026401SEQLIST.TXT, date recorded: Mar. 7, 2019, size: 7 KB).

BACKGROUND OF THE INVENTION

Interleukin-4 (IL-4) is a pleiotropic cytokine that has a broad spectrum of biological effects on lymphoid B and T cells, and many non-lymphoid cells including monocytes, endothelial cells and fibroblasts. For example, IL-4 induces the expression of class II major histocompatibility complex molecules on resting B cells, and enhances the secretion of IgG4 and IgE by human B cells. IL-4 is associated with a Th2-type immune response, and is produced by and promotes differentiation of Th2 cells. IL-4 has been implicated in a number of disorders, such as allergy and asthma.

IL-13 is a cytokine of 112 amino acids secreted by the activated T lymphocytes, the B lymphocytes and the mastocytes after activation (Minty, A. et al., Nature, 1993, 362, 248-250, and McKenzie, A. N. et al., Proc. Natl. Acad. Sci. U.S.A, 1993, 90, 3735-3739). By virtue of its numerous biological properties shared with IL-4, IL-13 has been described as an IL-4-like cytokine. Its activities are indeed similar to those of IL-4 on the B cells (Defrance, T. et al., J. Exp. Med., 1994, 179, 135-143, Punnonen, J. et al., Proc. Natl. Acad. Sci. (USA), 1993, 90, 3730-3734, Fior, R. et al., Eur. Cytokine Network, 1994, 5, 593-600), the monocytes (Muzio, M. R. F. et al., Blood, 1994, 83, 1738-1743, De Waal Malefyt, R. et al., J. Immunol, 1993, 151, 6370-6381, Doyle, A. et al., Eur. J. Immunol. 1994, 24, 1441-1445, Montaner, L. J. et al., J. Exp. Med., 1993, 178, 743-747, Sozzani, P. et al., J. Biol. Chem., 1995, 270, 5084-5088) and other non-haematopoietic cells (Herbert, J. M. et al., Febs Lett., 1993, 328, 268-270, and Derocq, J. M. et al., Febs Lett. 1994, 343, 32-36). On the other hand, contrary to IL-4, it does not exert a specific effect on resting or activated T cells (Zurawuki, G. et al., Immunol. Today, 1994, 15, 19-26).

Various biological activities of IL-13 on the monocytes/macrophages, the B lymphocytes and certain haematopoietic precursors have been described in detail by A. J. Minty as well as in review articles on IL-13. Several data indicate, in addition, that this cytokine has a pleiotropic effect on other cell types. These non-haematopoietic cells which are directly affected by IL-13 are endothelial and microglial cells, keratinocytes and kidney and colon carcinomas.

One of the stages in the analysis of the signal transmitted by a biological molecule within a cell consists in identifying its membrane receptor. The research studies carried out to this end on the IL-13 receptor have shown that IL-13 and IL-4 have a common receptor, or at the very least some of the components of a common receptor complex, as well as common signal transduction elements (Zurawski S. M. et al., EMBO J., 1993, 12, 2663-2670, Averse, G. et al., J. Exp. Med., 1993, 178, 2213-2218, Vita, N. et al., J. Biol. Chem., 1995, 270, 3512-3517, Lefort, S. et al., Febs Lett., 1995, 366, 122-126). This receptor is present at the surface of various cell types, in a variable number according to the cell type considered. The comparative distribution of the IL-13 and IL-4 receptors has been indicated by A. J. Minty (Interleukin-13 for Cytokines in Health and Disease. Eds D. G. Remick and J. S. Frie, Marcel Decker, N.Y. 1996).

The cell surface receptors and receptor complexes bind IL-4 and/or IL-13 with different affinities. The principle components of receptors and receptor complexes that bind IL-4 and/or IL-13 are IL-4Rα, IL-13Rα1 and IL-13Rα2. These chains are expressed on the surface of cells as monomers or heterodimers of IL-4Rα/IL-13Rα1 (Type II IL-4R) or IL-4Rα/c (Type I IL-4R). IL-4Rα monomer and IL-4Rα/c heterodimer bind IL-4, but not IL-13. IL-13Rα1 and IL-13Rα2 monomers bind IL-13, but do not bind IL-4. IL-4Rα/IL-13Rα1 heterodimer binds both IL-4 and IL-13 (Murata et al., Int. J. Hematol., 1999, 69, 13-20).

Th2-type immune responses promote antibody production and humoral immunity, and are elaborated to fight off extracellular pathogens. Th2 cells are mediators of Ig production (humoral immunity) and produce IL-4, IL-5, IL-6, IL-9, IL-10, and IL-13 (Tanaka, et al., Cytokine Regulation of Humoral Immunity, 251-272, Snapper, ed., John Wiley and Sons, New York (1996)). Th2-type immune responses are characterized by the generation of certain cytokines (e.g., IL-4, IL-13) and specific types of antibodies (IgE, IgG4) and are typical of allergic reactions, which may result in watery eyes and asthmatic symptoms, such as airway inflammation and contraction of airway muscle cells in the lungs.

Both IL-4 and IL-13 are therapeutically important cytokines based on their biological functions and play critical roles in many diseases. IL-4 has been shown to be able to inhibit autoimmune disease and IL-4 and IL-13 have both shown the potential to enhance anti-tumor immune responses. Elevations in IL-4 and IL-13 and their receptors have been linked to the pathogenesis of idiopathic pulmonary fibrosis (IPF) (Jakubzick et al., Am J Pathol. (2004) 164:1989-2001; Murray et al. Int J Biochem Cell Biol. (2008) 40:2174-82). Evidence in the literature demonstrates that the TH2 cytokines IL-4 and IL-13 play multiple roles in the pathogenesis of IPF as mediators of this lung tissue remodeling and fibrosis. Although the Th2-type CD4+ T cells in the lung are likely the predominant sources of IL-4 and IL-13, and are implicated as important regulators of extracellular matrix remodeling (Wynn, Nat. Rev. Immunol, (2004) 4:583-594), other cell types including mast cells, basophils, eosinophils, macrophages and epithelial cells may also be potential sources of these cytokines (Gordon and Martinez, Immunity Rev. (2010) 32: 593-604). In IPF patients, IL-13 and IL-4 levels in bronchial alveolar lavage fluid are elevated compared to normal controls. Such evidence suggests that therapies capable of suppressing or neutralizing these cytokines have the potential for delaying the progression of fibrosis in IPF patients. Since both cytokines are involved in the pathogenesis of allergic diseases or fibrotic diseases, inhibitors of these cytokines could provide therapeutic benefits.

Accordingly, a need exists for improved agents that inhibit IL-4, inhibit IL-13, and single agents that inhibit both IL-4 and IL-13 that are non-immunogenic and safe for use in humans.

SUMMARY OF THE INVENTION

The present invention provides certain advantages and advancements over the prior art. In one aspect, the invention provides safe doses in a human subject of a dual-V-region antibody-like protein or a fragment thereof that specifically binds to IL-4 and IL-13, wherein the dose comprises up to about 200 mg of the antibody-like protein or fragment thereof. In some embodiments, the human subject has idiopathic pulmonary fibrosis (IPF). In some embodiments, the safe dose comprises about 200 mg of the antibody-like protein or fragment thereof. In some embodiments, the safe dose comprises about 100 mg of the antibody-like protein or fragment thereof. In some embodiments, the safe dose comprises about 50 mg of the antibody-like protein or fragment thereof. In some embodiments, the safe dose is administered once weekly. In some embodiments, the safe dose is administered subcutaneously.

In another aspect, the invention provides methods of determining whether a dose comprising a dual-V-region antibody-like protein or a fragment thereof administered to a human subject specifically binds to IL-4 or IL-13 within the human subject, the method comprising: (a) administering the dose to the human subject; and (b) measuring the amount of TARC/CCL17 protein in a blood, plasma, or serum sample drawn from the human subject, wherein a decrease in the amount of TARC/CCL17 in the blood sample relative to an amount of TARC/CCL17 in the subject measured before the dose was administered signifies binding of the dual-V-region antibody-like protein or fragment thereof to IL-4 or IL-13. In some embodiments, the methods further comprise step (c): increasing or decreasing the dose depending on the magnitude of the decrease in TARC/CCL17 measured in step (b).

In some embodiments, step (c) further comprises increasing the dose if the decrease in TARC/CCL17 measured in step (b) is below a threshold value, or decreasing the dose if the decrease in TARC/CCL17 measured in step (b) is above a threshold value. In some embodiments, the threshold value of step (c) is about a 20% to about a 60% decrease in the amount of TARC/CCL17 relative to the amount of TARC/CCL17 in the subject measured before the dose was administered. In some embodiments, the threshold value is about a 40% to about a 50% decrease in the amount of TARC/CCL17 relative to the amount of TARC/CCL17 in the subject measured before the dose was administered. In some embodiments, the threshold value is about a 43% decrease in the amount of TARC/CCL17 relative to the amount of TARC/CCL17 in the subject measured before the dose was administered.

In some embodiments of the methods of determining, the dose is administered subcutaneously. In some embodiments, the amount of TARC/CCL17 is detected in step (b) by enzyme-linked immunosorbent assay (ELISA). In some embodiments, the human subject has idiopathic pulmonary fibrosis (IPF).

In another aspect, the invention provides a protein biomarker for binding of an antibody or antibody-like binding protein or fragment thereof to IL-4 or IL-13 or both in a human subject, wherein the biomarker is TARC/CCL17. In some embodiments, the antibody or antibody-like binding protein or fragment thereof is a dual-V-region antibody-like binding protein or fragment thereof. In some embodiments, the human subject has idiopathic pulmonary fibrosis (IPF).

In another aspect, the invention provides methods of treating idiopathic pulmonary fibrosis (IPF), comprising administering to a human subject with IPF up to 200 mg of a dual-V-region antibody-like binding protein or a fragment thereof. In some embodiments, the dual-V-region antibody-like binding protein or fragment thereof binds IL-4, IL-13, or both IL-4 and IL-13. In some embodiments, the dual-V-region antibody-like binding protein or fragment thereof is administered once per week. In some embodiments, the dual-V-region antibody-like binding protein or fragment thereof is administered subcutaneously.

In another aspect, the invention provides uses of a safe dose of a dual-V-region antibody-like binding protein or a fragment thereof for the treatment of idiopathic pulmonary fibrosis (IPF). In some embodiments, the safe dose is up to 200 mg of the dual-V-region antibody-like binding protein or a fragment thereof. In some embodiments, the safe dose is about 50 mg, or about 100 mg, or about 200 mg of the dual-V-region antibody-like binding protein or a fragment thereof. In some embodiments, the safe dose is administered subcutaneously. In some embodiments, the safe dose is administered once per week. In some embodiments, the dual-V-region antibody-like binding protein or a fragment thereof binds IL-4, IL-13, or both IL-4 and IL-13.

In another aspect, the invention provides safe doses of a dual-V-region antibody-like binding protein or a fragment thereof for the treatment of idiopathic pulmonary fibrosis (IPF). In some embodiments, the safe dose is up to 200 mg of the dual-V-region antibody-like binding protein or a fragment thereof. In some embodiments, the safe dose is about 50 mg, or about 100 mg, or about 200 mg of the dual-V-region antibody-like binding protein or a fragment thereof. In some embodiments, the safe dose is administered subcutaneously. In some embodiments, the safe dose is administered once per week. In some embodiments, the dual-V-region antibody-like binding protein or a fragment thereof binds IL-4, IL-13, or both IL-4 and IL-13.

BRIEF DESCRIPTION OF THE DRAWINGS

The following detailed description of the embodiments of the present invention can be best understood when read in conjunction with the following drawings, in which.

Figure 1:
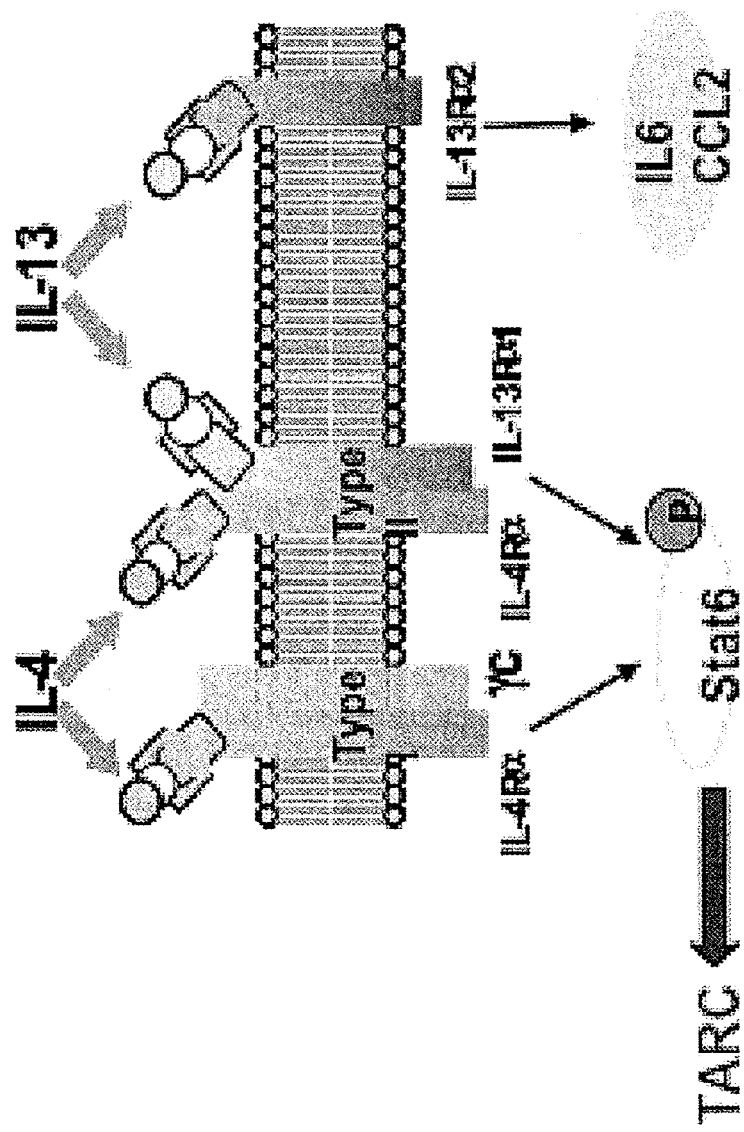
FIG. 1 shows the relationship of IL-4 and IL-13 to TARC/CCL17 signaling.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present invention.

DETAILED DESCRIPTION OF THE INVENTION

Unless otherwise defined, all technical and scientific terms used herein have the same meaning as commonly understood by one of ordinary skill in the art to which this invention belongs.

Each publication, patent application, patent, and other reference cited herein is explicitly incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

The following non-limiting definitions of some terms and phrases are provided to guide the artisan.

As used herein, the terms "polypeptide," "protein," and "peptide" are interchangeable and refer to a chain of amino acid monomers linked by peptide bonds. Typically, polypeptide chains are unbranched. As used herein, the terms "residue" and "protein residue" are interchangeable and refer to an amino acid that is bonded with other amino acids by one or more peptide bonds within a protein.

"Interleukin-4" (IL-4) relates to the naturally occurring, or endogenous mammalian IL-4 proteins and to proteins having an amino acid sequence which is the same as that of a naturally occurring or endogenous corresponding mammalian IL-4 protein {e.g., recombinant proteins, synthetic proteins (i.e., produced using the methods of synthetic organic chemistry)). Accordingly, as defined herein, the term includes mature IL-4 protein, polymorphic or allelic variants, and other isoforms of an IL-4 and modified or unmodified forms of the foregoing (e.g., lipidated, glycosylated). Naturally occurring or endogenous IL-4 includes wild type proteins such as mature IL-4, polymorphic or allelic variants and other isoforms and mutant forms which occur naturally in mammals (e.g., humans, non-human primates). Such proteins can be recovered or isolated from a source which naturally produces IL-4, for example. These proteins and proteins having the same amino acid sequence as a naturally occurring or endogenous corresponding IL-4, are referred to by the name of the corresponding mammal.

For example, where the corresponding mammal is a human, the protein is designated as a human IL-4. Several mutant IL-4 proteins are known in the art, such as those disclosed in WO 03/038041.

"Interleukin-13" (IL-13) refers to naturally occurring or endogenous mammalian IL-13 proteins and to proteins having an amino acid sequence which is the same as that of a naturally occurring or endogenous corresponding mammalian IL-13 protein (e.g., recombinant proteins, synthetic proteins (i.e., produced using the methods of synthetic organic chemistry)). Accordingly, as defined herein, the term includes mature IL-13 protein, polymorphic or allelic variants, and other isoforms of IL-13 (e.g., produced by alternative splicing or other cellular processes), and modified or unmodified forms of the foregoing (e.g., Hpidated, glycosylated). Naturally occurring or endogenous IL-13 include wild type proteins such as mature IL-13, polymorphic or allelic variants and other isoforms and mutant forms which occur naturally in mammals (e.g., humans, non-human primates). For example, as used herein IL-13 encompasses the human IL-13 variant in which Arg at position 110 of mature human IL-13 is replaced with Gin (position 110 of mature IL-13 corresponds to position 130 of the precursor protein) which is associated with asthma (atopic and nonatopic asthma) and other variants of IL-13. (Heinzmann et al, Hum Mol Genet. (2000) 9:549-559). Such proteins can be recovered or isolated from a source which naturally produces IL-13, for example. These proteins and proteins having the same amino acid sequence as a naturally occurring or endogenous corresponding IL-13 are referred to by the name of the corresponding mammal. For example, where the corresponding mammal is a human, the protein is designated as a human IL-13. Several mutant IL-13 proteins are known in the art, such as those disclosed in WO 03/035847.

In some aspects, the invention relates to the treatment of idiopathic pulmonary fibrosis (IPF). IL-4 and IL-13 are therapeutically important cytokines based on their biological functions and play critical roles in many diseases, including asthma (Curr Opin Allergy Clin Immunol 2005, Vo. 5, 161-166). IL-4 has been shown to be able to inhibit autoimmune disease and IL-4 and IL-13 have both shown the potential to enhance anti-tumor immune responses. Elevations in IL-4 and IL-13 and their receptors have been linked to the pathogenesis of idiopathic pulmonary fibrosis (IPF) (Jakubzick C. et al., Am J Pathol. 2004:164(6):1989-2001; Murray L A et al. Int J Biochem Cell Biol. 2008:40(10): 2174-82. Evidence in the literature demonstrate that the TH2 cytokines IL-4 and IL-13 play multiple roles in the pathogenesis of IPF as mediators of this lung tissue remodeling and fibrosis (Wynn, T A, Nat. Rev. Immunol, 4:583-594, 2004) and other cell types including mast cells, basophils, eosinophils, macrophages and epithelial cells may also be potential sources of these cytokines (Gordon S and Martinez F O, Immunity Rev. 32:593-604, 2010). In IPF patients, IL-13 and IL-4 levels in bronchial alveolar lavage fluid are elevated compared to normal controls. Such evidence suggests that therapies capable of suppressing or neutralizing these cytokines have the potential for delaying the progression of fibrosis in IPF patients. Since both cytokines are involved in the pathogenesis of allergic diseases or fibrotic diseases, inhibitors of these cytokines could provide therapeutic benefits.

The phrase "substantially identical" with respect to an antibody chain polypeptide sequence may be construed as an antibody chain exhibiting at least 70%, 80%, 90%, 95%, 96%, 97%, 98%, 99% or more sequence identity to the reference polypeptide sequence. The term with respect to a nucleic acid sequence may be construed as a sequence of nucleotides exhibiting at least about 85%, 90%, 95%, 96%, 97%, 98%, 99% or more sequence identity to the reference nucleic acid sequence. Identity can be determined by using any bioinformatics tool available to one skilled in the art. For example, Basic Local Alignment Search Tool (BLAST) is commonly employed to determine sequence identity (Altschul et al., Journal J. Mol. Biol. (1990) 215:403-410).

The terms, "identity" or "homology" may mean the percentage of nucleotide bases or amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "antibody" is used in the broadest sense, and specifically covers monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity. The antibodies of the invention can be of any class (e.g., IgG, IgE, IgM, IgD, IgA and so on), or subclass (e.g., $IgG_1$, $IgG_2$, $IgG_{2a}$, $IgG_3$, $IgG_4$, $IgA_1$, $IgA_2$ and so on) ("type" and "class", and "subtype" and ""subclass", are used interchangeably herein). Native or wildtype, that is, obtained from a non-artificially manipulated member of a population, antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at the other end. By "non-artificially manipulated" is meant not treated to contain or express a foreign antigen binding molecule. Wildtype can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-IL-4 antibody" means an antibody or polypeptide derived therefrom (a derivative) which binds specifically to IL-4 as defined herein, including, but not limited to, molecules which inhibit or substantially reduce the binding of IL-4 to its receptor or inhibit IL-4 activity.

As used herein, "anti-IL-13 antibody" means an antibody or polypeptide derived therefrom (a derivative) which binds specifically to IL-13 as defined herein, including, but not limited to, molecules which inhibit or substantially reduce the binding of IL-13 to its receptor or inhibit IL-13 activity.

The term "variable" in the context of a variable domain of antibodies refers to certain portions of the pertinent molecule which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat et al., unless otherwise indicated. One CDR can carry the ability to bind specifically to the cognate epitope.

The term "hinge" or "hinge region" as used in the present invention refers to the flexible polypeptide comprising the amino acids between the first and second constant domains of an antibody.

The phrases and terms "fragment," "functional fragment," "variant," "derivative," or "analog" and the like, as well as forms thereof, of an antibody, antigen, or antigen-binding protein is a compound or molecule having qualitative biological activity in common with a full-length antibody or antigen of interest. For example, a functional fragment or analog of an anti-IL-4 antibody is one that can bind to an IL-4 molecule, or that can prevent or substantially reduce the ability of a ligand, or an agonistic or antagonistic antibody, to bind to IL-4.

In addition, the terms "fragment" and "antibody fragment" refer to a portion of an intact or a full-length chain or an antibody, generally the target binding or variable region. Examples of antibody fragments include, but are not limited to, $F_{ab}$, $F_{ab'}$, $F_{(ab')2}$ and $F_v$ fragments. For example, a fragment or analog of an anti-IL-4 and/or IL-13 antibody is one which can prevent or substantially reduce the ability of the receptor to bind to a ligand or to initiate signaling. As used herein, "fragment," "functional fragment," and "antibody fragment" generally are synonymous and, with respect to antibodies, can refer to fragments, such as $F_v$, $F_{ab}$, $F_{(ab')2}$ and so on which can prevent or substantially reduce the ability of the receptor to bind to a ligand or to initiate signaling.

An "$F_v$" fragment consists of a dimer of one heavy and one light chain variable domain in a non-covalent association ($V_H$-$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an $F_v$ comprising only three CDRs specific for a target) can have the ability to recognize and to bind a target.

"Single-chain $F_v$," "s$F_v$," or "scAb" antibody fragments comprise the $V_H$ and $V_L$ domains of an antibody, wherein these domains are present in a single polypeptide chain. Generally, the $F_v$ polypeptide further comprises a polypeptide linker, often a flexible molecule, between the $V_H$ and $V_L$ domains, which enables the sFv to form the desired structure for target binding.

The term "diabody" refers to an antibody fragment with two antigen-binding sites, which can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with binding domains on another peptide chain to create two antigen-binding sites.

An "$F_{ab}$" fragment contains the variable and constant domains of the light chain and the variable and first constant domain ($C_{H1}$) of the heavy chain. $F_{ab'}$ fragments differ from $F_{ab}$ fragments by the addition of a few residues at the carboxyl terminus of the $C_{H1}$ domain to include one or more cysteines from the antibody hinge region. $F_{ab'}$ fragments can be produced by cleavage of the disulfide bond at the hinge cysteines of the $F_{(ab')2}$ pepsin digestion product. Additional enzymatic and chemical treatments of antibodies can yield other functional fragments of interest.

The term "linear Fab" refers to a tetravalent antibody as described by Miller et al. (2003), J Immunol. 170: 4854-4861. A linear Fab is composed of a tandem of the same CH1-VH domain, paired with the identical light chain at each CH1-VH position. These molecules have been developed in order to increase the valency of an antibody to enhance its functional affinity through the avidity effect, but they are monospecific.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as they exhibit the desired biological activity of binding to IL-4 and/or IL-13 or impacting IL-4 and/or IL-13 activity or metabolism (U.S. Pat. No. 4,816,567; and Morrison et al. (1984), Proc Natl Acad Sci USA 81:6851). Thus, CDRs from one class of antibody can be grafted into the FR of an antibody of different class or subclass.

Monoclonal antibodies are highly specific, being directed against a single target site, epitope or determinant. Furthermore, in contrast to conventional (polyclonal) antibody preparations which typically include different antibodies directed against different determinants (epitopes) of an antigen, each monoclonal antibody is directed against a single determinant on the target. In addition to their specificity, monoclonal antibodies are advantageous being synthesized by a host cell, uncontaminated by other immunoglobulins, and provides for cloning the relevant gene and mRNA encoding the antibody of chains thereof. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using well known techniques or can be purified from a polyclonal preparation. The parent monoclonal antibodies to be used in accordance with the present invention may be made by the hybridoma method described by Kohler et al. (1975), Nature 256:495, or may be made by recombinant methods well known in the art.

The term "polyvalent antibody" as used in the present invention refers to an antibody comprising two or more antigen binding sites, thus being able to bind two or more antigens, which may have the same or a different structure, simultaneously. The term "bivalent" means that the antibody comprises two antigen binding sites. The term "tetravalent" means that the antibody comprises four antigen binding sites.

The term "antigen binding site" as used in the present invention refers to the part of the antibody which comprises the area which specifically binds to and is complementary to part or all of an antigen. Where an antigen is large, an antibody may only bind to a particular part of the antigen, which part is termed on epitope. An antigen binding domain may be provided by one or more antibody variable domains. Preferably, an antigen binding domain is made of the association of an antibody light chain variable domain (VL) and an antibody heavy chain variable domain (VH).

The term "antigen" as used in the present invention refers to a molecule or a portion of a molecule capable of being bound by the antibodies of the present invention. An antigen can have one or more than one epitope. Examples of antigens recognized by the antibodies of the present invention include, but are not limited to, serum proteins, e.g. cytokines such as IL-4, IL-5, IL-9 and IL-13, bioactive peptides, cell surface molecules, e.g. receptors, transporters, ion-channels, viral and bacterial proteins.

The term "monospecific" as used in the present invention means that the polyvalent antibody of the present invention recognizes only one antigen, all the antigen binding sites being identical.

The term "bispecific" as used in the present invention means that the polyvalent antibody of the present invention recognizes two different epitopes on the same or on two different antigens.

The term "bispecific antibody" (BsAb) refers to molecules which combine the antigen-binding sites of two antibodies within a single molecule. Thus, a bispecific antibody is able to bind two different antigens simultaneously. Besides applications for diagnostic purposes, BsAbs pave the way for new therapeutic applications by redirecting potent effector systems to diseased areas or by increasing neutralizing or stimulating activities of antibodies.

It has been of interest to produce bispecific antibodies (BsAbs) which combine the antigen-binding sites of two antibodies within a single molecule. Thus, such a molecule would be able to bind two different antigens simultaneously. Besides applications for diagnostic purposes, they pave the way for new therapeutic applications, e.g. by redirecting potent effector systems to diseased areas (where cancerous cells often develop mechanisms to suppress normal immune responses triggered by monoclonal antibodies, like antibody-dependent cellular cytotoxicity (ADCC) or complement-dependent cytotoxicity (CDC)), or by increasing neutralizing or stimulating activities of antibodies. Initial attempts to couple the binding specificities of two whole antibodies against different target antigens for therapeutic purposes utilized chemically fused heteroconjugate molecules (Staerz et al (1985), Nature 314: 628-631).

Bispecific antibodies were originally made by fusing two hybridomas, each capable of producing a different immunoglobulin (Milstein and Cuello, 1983, 1984), but the complexity of species (up to ten different species) produced in cell culture makes purification difficult and expensive (George and Huston, 1997). Despite the promising results obtained using heteroconjugates or bispecific antibodies produced from cell fusions as cited above, several factors made them impractical for large scale therapeutic applications. Such factors include: rapid clearance of heteroconjugates in vivo, the laboratory intensive techniques required for generating either type of molecule, the need for extensive purification of heteroconjugates away from homoconjugates or mono-specific antibodies and generally low yields.

Genetic engineering has been used with increasing frequency to design, modify, and produce antibodies or antibody derivatives with a desired set of binding properties and effector functions. A variety of recombinant methods have been developed for efficient production of BsAbs, both as antibody fragments (Carter et al. (1995), J. Hematotherapy 4: 463-470; Pluckthun et al. (1997) Immunotechology 3: 83-105; Todorovska et al. (2001) J. Immunol. Methods 248: 47-66) and full length IgG formats (Carter (2001) J. Immunol. Methods 248: 7-15).

Abbott described in US patent U.S. Pat. No. 7,612,181 a murine Dual-Variable-Domain IgG (DVD-IgG) bispecific antibody, which is based on the dual-Fv format described in Unilever patent (U.S. Pat. No. 5,989,830). A humanized bispecific format was described in WO2009/052081 (TBTI) which is incorporated herein by reference in its entirety. The addition of constant domains to respective chains of the Dual-Fv (CH1-Fc to the heavy chain and kappa or lambda constant domain to the light chain) led to functional bispecific dual-V-region antibody like binding proteins.

A bispecific dual-variable-region (dual-V-region) antibody-like binding protein having four binding sites that specifically bind to IL-4 and IL-13 has been reported in International Applications No. PCT/US2008/079787 (WO 2009/052081) and PCT/US2012/029147 (WO 2012/125775), both of which are incorporated by reference herein in their entirety.

An embodiment of the invention is a bispecific antibody that has been engineered to comprise a dual-V-region antibody-like protein or fragment thereof that specifically binds to two different epitopes on the same or on two different antigens. An embodiment of the invention a bispecific antibody or bispecific antibody fragment thereof that specifically binds to IL-13 and IL-4, wherein said bispecific antibody or bispecific antibody fragment thereof comprises a variable light chain domain and a variable heavy chain domain, wherein said variable light chain domain comprises amino acid sequences SEQ ID NO:1 and SEQ ID NO:3. A further embodiment of the invention is a bispecific antibody or bispecific antibody fragment thereof that specifically binds to IL-13 and IL-4, wherein said bispecific antibody or bispecific antibody fragment thereof comprises a variable light chain domain and a variable heavy chain domain, wherein said variable heavy chain domain comprises amino acid sequences SEQ ID NO:2 and SEQ ID NO:5. Another embodiment of the invention is a bispecific antibody or bispecific antibody fragment thereof that specifically binds to IL-13 and IL-4, wherein said bispecific antibody or bispecific antibody fragment thereof comprises a variable light chain domain and a variable heavy chain domain, wherein said variable heavy chain domain comprises amino acid sequences SEQ ID NO:2 and SEQ ID NO:4. An embodiment of the invention is a bispecific antibody or bispecific antibody fragment thereof that specifically binds to IL-13 and IL-4, wherein said bispecific antibody or bispecific antibody fragment thereof comprises a variable light chain domain comprising amino acid sequences SEQ ID NO:1 and SEQ ID NO:3, and a variable heavy chain domain comprising amino acid sequences SEQ ID NO:2 and SEQ ID NO:4. A further embodiment of the invention is a bispecific antibody or bispecific antibody fragment thereof that specifically binds to IL-13 and IL-4, wherein said bispecific antibody or bispecific antibody fragment thereof comprises a variable light chain domain comprising amino acid sequences SEQ ID NO:1 and SEQ ID NO:3, and a variable heavy chain domain comprising amino acid sequences SEQ ID NO:2 and SEQ ID NO:4, wherein a peptide linker links SEQ ID NO:1 to SEQ ID NO:3, and a peptide linker links SEQ ID NO:2 to SEQ ID NO:4.

An embodiment of the invention is huTBTI3_2_1 or SAR156597 comprising a bispecific antibody or bispecific antibody fragment thereof that specifically binds to IL-13 and IL-4, comprising (a) variable light chain domain comprising the amino acid sequences of SEQ ID NO:1 and SEQ ID NO:3; (b) a variable heavy chain domain comprising the amino acid sequences of SEQ ID NO:2 and SEQ ID NO:4; (c) a peptide linker linking SEQ ID NO:1 to SEQ ID NO:3, and a peptide linker linking SEQ ID NO:2 to SEQ ID NO:4 wherein the peptide linker has an amino acid sequence consisting of SEQ ID NO:6; and (d) constant region domains.

The term "multispecific" as used in the present invention means that the polyvalent antibody of the present invention recognizes multiple different epitopes on the same or on multiple different antigens.

The term "linker" as used in the present invention refers to a peptide adapted to connect the variable domains of the antibody constructs of the present invention. The peptide linker may contain any amino acids, the amino acids glycine (G) and serine (S) being preferred. The linkers may be equal or differ from each other between and within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19 or 20 amino acids. A preferred peptide linker unit for the heavy chain domains as for the light chain domains is GGGGS. The numbers of linker units of the heavy chain and of the light chain may be equal (symmetrical order) or differ from each other (asymmetrical order).

A peptide linker is preferably long enough to provide an adequate degree of flexibility to prevent the antibody moieties from interfering with each others activity, for example by steric hindrance, to allow for proper protein folding and, if necessary, to allow the antibody molecules to interact with two or more, possibly widely spaced, receptors on the same cell; yet it is preferably short enough to allow the antibody moieties to remain stable in the cell.

Therefore, the length, composition and/or conformation of the peptide linkers can readily be selected by one skilled in the art in order to optimize the desired properties of the polyvalent antibody.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies) which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_e$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to IL-4 and/or IL-13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., Prot Eng 7(6)805-814, 1994; Mol Imm 44:1986-1988, 2007; Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333 and U.S. Pat. No. 5,869,619.

"Antibody homolog" or "homolog" refers to any molecule which specifically binds IL-4 and/or IL-13 as taught herein. Thus, an antibody homolog includes native or recombinant antibody, whether modified or not, portions of antibodies that retain the biological properties of interest, such as binding IL-4 or IL-13, such as an $F_{ab}$ or $F_v$ molecule, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of a IL-4, IL-13 or bispecific IL-4/IL-13 antibody of the present invention. Preferably, homology is with the amino acid sequence of the variable regions of an antibody of the present invention. "Sequence homology" as applied to an amino acid sequence herein is defined as a sequence with at least about 90%, 91%, 92%, 93%, 94%, 95%, 96%, 97%, 98% or 99% sequence homology to another amino acid sequence, as determined, for example, by the FASTA search method in accordance with Pearson & Lipman, Proc Natl Acad Sci USA 85, 2444-2448 (1988).

A chimeric antibody is one with different portions of an antibody derived from different sources, such as different antibodies, different classes of antibody, different animal species, for example, an antibody having a variable region derived from a murine monoclonal antibody paired with a human immunoglobulin constant region and so on. Thus, a humanized antibody is a species of chimeric antibody. Methods for producing chimeric antibodies are known in the art, see, e.g., Morrison, 1985, Science 229:1202; Oi et al., 1986, BioTechniques 4:214; Gillies et al., 1989, J Immunol Methods 125:191-202; and U.S. Pat. Nos. 5,807,715, 4,816, 567, and 4,816,397.

Artificial antibodies include scFv fragments, chimeric antibodies, diabodies, triabodies, tetrabodies and molecular recognition units (mrus) (see reviews by Winter & Milstein, 1991, Nature 349:293-299; and Hudson, 1999, Curr Opin Imm 11:548-557), each with antigen-binding or epitope-binding ability. In the single chain $F_v$ fragment (scF$_v$), the $V_H$ and $V_L$ domains of an antibody are linked by a flexible peptide. Typically, the linker is a peptide of about 15 amino acids. If the linker is much smaller, for example, 5 amino acids, diabodies are formed. The smallest binding unit of an antibody is a CDR, typically the CDR2 of the heavy chain which has sufficient specific recognition and binding capacity. Such a fragment is called a molecular recognition unit or mru. Several such mrus can be linked together with short linker peptides, therefore forming an artificial binding protein with higher avidity than a single mru.

Also included within the scope of the invention are functional equivalents of an antibody of interest. The term "functional equivalents" includes antibodies with homologous sequences, antibody homologs, chimeric antibodies, artificial antibodies and modified antibodies, for example, wherein each functional equivalent is defined by the ability to bind to IL-4 and/or IL-13, inhibiting IL-4 and/or IL-13 signaling ability or function, or inhibiting binding of IL-4 and/or IL-13 to its receptor. The skilled artisan will understand that there is an overlap in the group of molecules termed "antibody fragments" and the group termed "functional equivalents." Methods of producing functional equivalents which retain IL-4 and/or IL-13 binding ability are known to the person skilled in the art and are disclosed, for example, in WO 93/21319, EPO Ser. No. 239,400, WO 89/09622, EPO Ser. No. 338,745 and EPO Ser. No. 332,424.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein etc. The covalent attachment need not yield an antibody that is immune from generating an anti-idiotypic response. The modifications may be achieved by known techniques, including, but not limited to, specific chemical cleavage, acetylation, formylation, metabolic synthesis etc. Additionally, the modified antibodies may contain one or more non-classical amino acids.

"Mammal" for purposes of treatment refers to any animal classified as a mammal, including human, domestic and farm animals, nonhuman primates, and zoo, sports or pet animals, such as dogs, horses, cats, cows etc.

The term "treatment" as used in the present invention refers to both therapeutic treatment and prophylactic or preventative measures as a course of therapy. It refers to preventing, curing, reversing, attenuating, alleviating, minimizing, suppressing or halting deleterious effects of a disease state, disease progression, disease causative agent (e.g., bacteria or viruses) or other abnormal condition.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5% or 1%, (by dry weight) of contaminating protein. When the antibody is recombinantly produced, it is also preferably substantially free of culture medium, i.e., culture medium represents less than about 20%, 10%, 5%, 2.5% or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 30%, 20%, 10%, 5% or 1% (by dry weight) of chemical precursors or compounds other than antibody of interest. In a preferred embodiment of the present invention, antibodies are isolated or purified.

As used herein, the terms "therapeutic agent" and "therapeutic agents" refer to any agent(s) which can be used in the treatment, management or amelioration of a disease, disorder, malady and the like associated with aberrant IL-4 and/or IL-13 metabolism and activity.

As used herein, "dose" refers to the quantity of any agent(s) which can be used in the treatment, management or amelioration of a disease, disorder, malady and the like associated with aberrant IL-4 and/or IL-13 metabolism and activity.

As used herein, "safe dose" refers to any agent(s) or dose of any agent(s) which can be used in the treatment, management or amelioration of a disease, disorder, malady and the like associated with aberrant IL-4 and/or IL-13 metabolism and activity while maintaining a clinically acceptable benefit/risk profile. A safe dose of the dual-V-region antibody-like binding proteins or fragments thereof disclosed herein is selected from the group consisting of 10 mg, 20 mg, 40 mg, 50 mg, 80 mg, 100 mg, 150 mg, 200 mg, and 300 mg. An embodiment of a safe dose is about 10 mg to about 300 mg. A further embodiment of a safe dose of a is any dose that is 200 mg, about 200 mg, up to 200 mg, or no greater than about 200 mg. In other embodiments, a safe dose is about 50 mg, or about 100 mg, or about 200 mg. In some embodiments, the safe dose is administered once weekly. In some embodiments, the safe dose is administered subcutaneously (SC).

Intracellular signaling after ligation of IL-4 and IL-13 with their cell surface receptors is mediated in part by phosphorylation of the signaling molecule signal transducer and activator of transcription 6 (Stat6).

Chemokine (C-C motif) ligand 17 (CCL17) is a small cytokine belonging to the CC chemokine family. CCL17 is also known as thymus and activation regulated chemokine (TARC). TARC is induced by IL-4 and/or IL-13 through Stat6 phosphorylation (Wirnsberger et al., (2006) Eur J Immunol. 36: 1882-91; Liddiard et al., (2006) BMC Mol Biol. 29: 7:45; Monick et al., (2007) J Immunol. 179:1648-58) Thus, inhibition of IL-4 and/or IL-13-mediated signaling by, for example, IL-4/IL-13-binding antibody-like proteins, is correlated with inhibition of TARC inducement. In some embodiments, the methods disclosed herein comprise methods of detecting the binding to IL-4 and/or IL-13 of an antibody or antibody-like binding protein or fragment thereof that has been administered to a subject, the methods comprising (a) administering the antibody or antibody-like binding protein of fragment thereof to the subject; and (b) determining the amount of CCL17/TARC within a blood, serum, or plasma sample drawn from the subject, wherein a decrease in the amount of CCL17/TARC in the sample relative to a sample drawn from the subject prior to administration of the antibody or antibody-like binding protein or fragment thereof signifies binding of the antibody or antibody-like binding protein or fragment thereof to IL-4 and/or IL-13. In some embodiments, the subject is a human subject. In some embodiments, the antibody or antibody-like binding protein or fragment thereof is a dual-V-region antibody-like binding protein or fragment thereof. In some embodiments, the dual-V-region antibody-like binding protein or fragment thereof is specific for IL-4 or IL-13, or bispecific for IL-4 and IL-13. In some embodiments, step (c) further comprises increasing the dose if the decrease in TARC/CCL17 measured in step (b) is below a threshold value (i.e. if TARC/CCL17 levels do not decrease enough), or decreasing the dose if the decrease in TARC/CCL17 measured in step (b) is above a threshold value (i.e. if TARC/CCL17 decreases too much). In some embodiments, the threshold value of step (c) is about a 10% decrease, or about a 15% decrease, or about a 20% decrease, or about a 25% decrease, or about a 30% decrease, or about a 35% decrease, or about a 40% decrease, or about a 45% decrease, or about a 50% decrease, or about a 55% decrease, or about a 60% decrease, or about a 65% decrease in the amount of TARC/CCL17 relative to the amount of TARC/CCL17 in the subject measured before the dose was administered. In some embodiments, the threshold value is about a 20% to about a 60% decrease, or about a 40% to about a 50% decrease in the amount of TARC/CCL17 relative to the amount of TARC/CCL17 in the subject measured before the dose was administered. In some embodiments, the threshold value is about a 43% decrease in the amount of TARC/CCL17 relative to the amount of TARC/CCL17 in the subject measured before the dose was administered. For example, a 43% decrease for a 200 mg dose signifies binding of a 200 mg dose of bispecific anti-IL-4/IL-13 dual-V-region antibody-like binding protein to IL-4/IL-13.

The term "about" when used in connection with a numerical value is meant to encompass numerical values within a range having a lower limit that is 5%, 10%, or 15% smaller than the indicated numerical value and having an upper limit that is 5%, 10%, or 15% larger than the indicated numerical value.

EXAMPLES

The Examples that follow are illustrative of specific embodiments of the invention, and various uses thereof. They are set forth for explanatory purposes only, and are not to be taken as limiting the invention.

The terms "huTBTI3_2_1" and "SAR156597" are interchangeable and refer to the same dual-V-region antibody-like protein comprising a variable light chain comprising amino acid sequences SEQ ID NO:1 and SEQ ID NO:3 and a variable heavy chain comprising amino acid sequences SEQ ID NO:2 and SEQ ID NO:4.

Example 1: Clinical Study Format

A multi-center, randomized, double-blind, placebo-controlled clinical study was conducted to assess the safety and tolerability of repeated doses of SAR156597 administered subcutaneously (SC) once weekly over a 6-week period in up to 3 sequential, ascending dose cohorts of patients with idiopathic pulmonary fibrosis (IPF). IPF is a progressive, diffuse, and distinct chronic fibrosing interstitial pneumonia of unknown cause that is uniformly fatal with a median survival of 2 to 3 years.

In each dose cohort, 8 patients (6 receiving SAR156597 and 2 receiving placebo) received repeated SC, once-weekly doses of SAR156597 or matching placebo control. The second cohort was initiated after the review of the safety of the first cohort by the DMC. The third cohort at a dose of 200 mg was initiated after the review of the safety of the 2 preceding cohorts.

For each patient, the study duration was 22 weeks, as follows: 4 weeks of screening; 6 weeks of treatment period (7 administrations); 12 weeks follow-up.

If, at Week 12, the anti-drug antibodies (ADAs) related to immunogenicity were present, an additional follow-up visit occurred at a minimum of 6 months after the first dose to examine the elevated parameter. The end of the clinical trial was defined as the day the last patient completed his/her last visit planned in the protocol.

Selection of Study Population.

Patients were included in the study according to the following criteria.

Inclusion Criteria

Adult (aged>18 years) male or female patients.

Documented diagnosis of IPF according to the current AMERICAN THORACIC SOCIETY (ATS)/THE EUROPEAN RESPIRATORY SOCIETY (ERS)/THE JAPANESE RESPIRATORY SOCIETY (JRS)/THE LATIN AMERICAN THORACIC ASSOCIATION (ALAT) guidelines, i.e. exclusion of other known causes of interstitial lung disease (e.g. domestic and occupational environmental exposures, connective tissue disease, and drug toxicity); AND either (1) Presence of a usual interstitial pneumonitis pattern on high-resolution computed tomography (HRCT) in patients not subjected to surgical lung biopsy; OR (2) Specific combinations of HRCT and surgical biopsy pattern in patients subjected to surgical lung biopsy.

Written, signed, and dated informed consent obtained prior to any procedure related to the study.

Exclusion Criteria

Forced vital capacity <50% of predicted value.

Carbon monoxide diffusing lung capacity (corrected for hemoglobin) <35% predicted value.

Oxygen saturation <90% by pulse oximetry while breathing ambient air at rest (sitting position for 10 minutes).

Known diagnosis of significant respiratory disorders (e.g. hyper-reactive airway disease, tuberculosis, sarcoidosis, aspergillosis, emphysema or chronic obstructive pulmonary disease [COPD], or cystic fibrosis) other than IPF.

Active vasculopathy or use of vasoactive drugs (e.g. phosphodiesterase 4 inhibitors, calcineurin inhibitors, tacrolimus, cyclosporine).

Known HIV or chronic viral hepatitis.

Patients with active tuberculosis or latent tuberculosis infection (Exclusion related to tuberculosis: Active tuberculosis or a history of incompletely treated tuberculosis; Positive QuantiFERON-TB Gold® test at screening (regardless of prior treatment status); Clinically significant abnormality consistent with prior/active tuberculosis infection based upon chest radiograph with at least posterior-anterior view (radiograph must be taken within 12 weeks prior to screening visit or during the screening period). Additional lateral view is recommended but not required. Patients who reactivated latent tuberculosis infection during previous tumor necrosis factor-α (TNF-α)-antagonist or other non-anti-TNF-α bioDMARD treatment, regardless of subsequent appropriate anti-tuberculosis treatment. Suspected extra-pulmonary tuberculosis infection; Patients at high risk of contracting tuberculosis, such as close contact with individuals with active or latent tuberculosis.).

Evidence of any clinically significant, severe or unstable, acute or chronically progressive medical (other than IPF) or surgical disorder, or any condition that may affect patient safety in the judgment of the investigator.

Clinically significant abnormal electrocardiogram (ECG) (including QTc 500 ms) at screening.

Clinically significant laboratory tests at screening: Alanine transaminase (ALT) or aspartate transaminase (AST) >2 times upper limit of normal range (ULN); Hemoglobin <12 g/100 mL for male and <11 g/100 mL for female; Neutrophils <1500/mm$^3$ (except <1000/mm$^3$ for those of African descent); Platelets <150 000/mm$^3$; Creatinine 150 μmol/L.

Current history of substance and/or alcohol abuse.

Females who are lactating or who are pregnant.

Woman of childbearing potential (less than two years postmenopausal or not surgically sterile), with a positive urine beta-human chorionic gonadotropin (β-HGC) pregnancy test at screening and not using an acceptable form of contraception (e.g. birth control pill, intra uterine device, implants, injection of Depo-Provera™, double-barrier method, abstinence, vasectomized partner—unless not acceptable by the local Health Authorities).

Use of any registered therapy targeted to treat IPF within 4 weeks prior to screening.

Use of any cytotoxic/immunosuppressive agent including but not limited to azathioprine, cyclophosphamide, methotrexate and cyclosporine within 4 weeks prior to screening.

Use of any cytokine modulators (etanercept, adalimumab, efalizumab, infliximab, golimumab, certolizumab, rituximab) within 12 weeks or 5 half-lives of screening (24 weeks for rituximab and 24 months for alefacept).

Use of any investigational drug within one month of screening, or 5 half-lives, if known (whichever is longer).

The investigational medicinal product (IMP) was provided as SAR156597 in lyophilized form for the preparation of SC dose solution. Each vial containing 185 mg of SAR156597 plus excipients was stored between 2° C. and 8° C. (36° F. and 46° F.). The IMP was reconstituted on the morning of dosing (no more than 1 hour prior to SC injection) with 1.7 mL sterile, nonpyrogenic distilled water at room temperature. The concentrations of the constituents in solution after reconstitution for injection were: 100 mg/mL of SAR156597 in 6.3 mmol/L monobasic sodium phosphate, 3.7 mmol/L tromethamine, 5% (weight/volume) sucrose, 3% (w/V) proline, and 0.2% (w/V) polysorbate 80 with a final pH of 7.0.

For placebo, each vial containing 2 mL of liquid containing the same excipients at the same concentrations as for the reconstituted SAR156597 formulation was provided.

One-mL syringes were used for delivering volumes of 1.0 mL or less; and syringes graduated to deliver 2 to 3 mL were used for delivering volumes greater than 1 mL. A summary of required volumes needed for the various planned dose levels is shown in Table 1.

TABLE 1

| Planned SAR156597 subcutaneous administration | | | |
|---|---|---|---|
| Group | Dose (mg) | Total injected | volume |
| 1 | 50 | 0.5 mL | |
| 2 | 100 | 1.0 mL | |
| 3 | ≤200 | ≤2.0 mL | |

The IMP (SAR156597 or placebo) was administered as periumbilical SC injections. Within 1 hour of reconstitution, the dose was administered in a zone 4 to 10 cm from the umbilicus in a left or right quadrant above the waistline.

Selection of Doses in the Study

SAR156597 is an engineered humanized bi-specific immunoglobin G (IgG)-4 antibody that binds and neutralizes both IL-4 and IL-13. SAR156597 shows high affinity for IL-4 and IL-13 from both humans and cynomolgus monkeys.

For each patient, once weekly SC dose for 6 weeks was administered (a total of 7 administrations) and the dose escalation in Cohorts 1 to 3 was performed as follows: SAR156597 at 50 mg (0.5 mL) for Cohort 1, SAR156597 at 100 mg (1 mL) for Cohort 2, and SAR156597 at 200 mg (2.0 mL) for Cohort 3, all with matching placebo.

Example 2: Pharmacodynamics (PD) Evaluations

The effect of repeated ascending doses of SAR156597 was evaluated on pulmonary function tests (PFTs), respiratory symptoms, and on selected biomarkers. More specifically, the following PD variables were evaluated:

1. Pulmonary function test (PFT): Carbon monoxide diffusing capacity, corrected for hemoglobin (DLCO); Forced (expiratory) vital capacity (FVC); Forced expiratory volume over 1 second (FEV1); Total lung capacity (body plethysmography) (TLC); Residual volume (body plethysmography) (RV). Two PFTs were performed within 3 weeks prior to dosing. The first PFT was performed to screen the patient and the data from the second PFT (at the randomization visit) was averaged with the first one to establish a baseline value; these tests were performed on separate days. A PFT was also performed at Visit 8 (Week 6)/end-of-treatment (EOT) and Visit 14 (Week 18/12 weeks following the last dose of study treatment).

2. Oxygen saturation was assessed using SpO2 at screening, baseline, at Week 6/EOT, and at Week 18 (12 weeks following the last dose of study treatment). The first SpO2 measurement was performed at the screening and the data from the second measurement was averaged with the first one to establish a baseline value; these tests were performed on separate days.

3. Impact of IPF on quality of life (QoL) was assessed using the St. George's Respiratory Questionnaire (SGRQ) at baseline, at Week 6/EOT, and at Week 18 (12 weeks following the last dose of study treatment).

4. Selected biomarkers from whole blood were assessed at screening, baseline, Week 6/EOT, and at the end of the follow-up period (Week 18). Serum and plasma samples were collected at screening, baseline (prior to first dosing), Week 6/EOT, and at the end of the follow-up period (Week 18). The methodology for sample preparation and analysis was as follows: For each serum sample, 3 mL of blood was collected into dry tubes without clot activator. After 1 hr at room temperature the tubes were centrifuged at 3000 g for 15 minutes at +4° C. and the serum was aliquoted and stored at −70° C. until use. For each plasma sample, 4.5 mL of blood was collected in Na-citrate tubes and mixed immediately by gently inverting the tube 10 times. Tubes were centrifuged at 2000 g for 15 minutes and plasma was aliquoted and stored at −70° C. until use. TARC was quantified using a human CCL17/TARC Quantikine ELISA kit from R&D Systems, following the instructions of the kit manual. For this assay, the lower limit of quantification was 31.2 pg/mL and the upper limit of quantification was 2000 pg/mL. Some archival samples were prepared and stored for future use in getting more knowledge on biomarkers by using assays that could emerge after the completion of the study. Protein biomarkers included chemokine [C-C motif] ligand 18 [CCL-18], Krebs von den Lundgen-6 [KL-6], surfactant protein A [SP-A], surfactant protein D [SP-D], mammalian chitinase-like proteins [YKL-40], IL-4, IL-13, IL-8, immunoglobin E [IgE], eotaxin, inter-cellular adhesion molecule 1 [ICAM1], periostin, thymus and activation-regulated chemokine [TARC] CCL-17, matrix metalloproteinase-7 [MMP7]), and RNA (mRNA, micro-RNA) expressions.

Pharmacodynamics Results

PD endpoints: The changes from baseline in the 5 PFTs (FVC, FEV1, TLC, DLCO, and RV) were analyzed. At the end of treatment (EOT, at Visit 8, Week 6), the patient lung function was overall not altered as evident by the mean change from baseline for the main parameters (percent predicted FVC and percent predicted DLCO) which was comparable between treatment groups.

Twelve weeks after the EOT, the mean change from baseline for % predicted FVC and % predicted DLCO showed that lung function remained unchanged in all treatment groups.

Secondary PD endpoints: Secondary PD variables (SpO2, protein/RNA biomarkers, and the SGRQ) were measured at the end of the 6-week treatment and post-treatment follow-up periods. These PD results were inconclusive due to the small sample size of the study and the short treatment duration.

Figure 2:
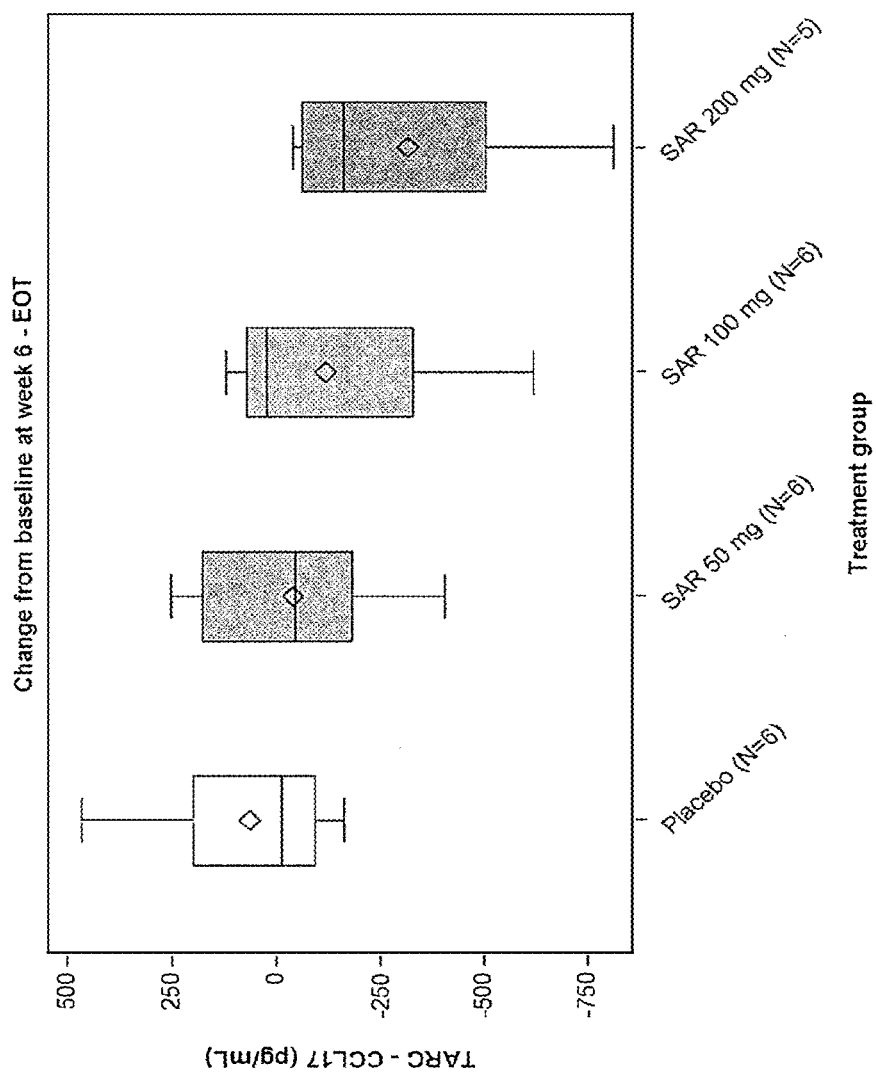
FIG. 2 shows a trend of reduced TARC/CCL17 expression in the blood of human subjects with increasing doses of SAR156597.
Figure 3:
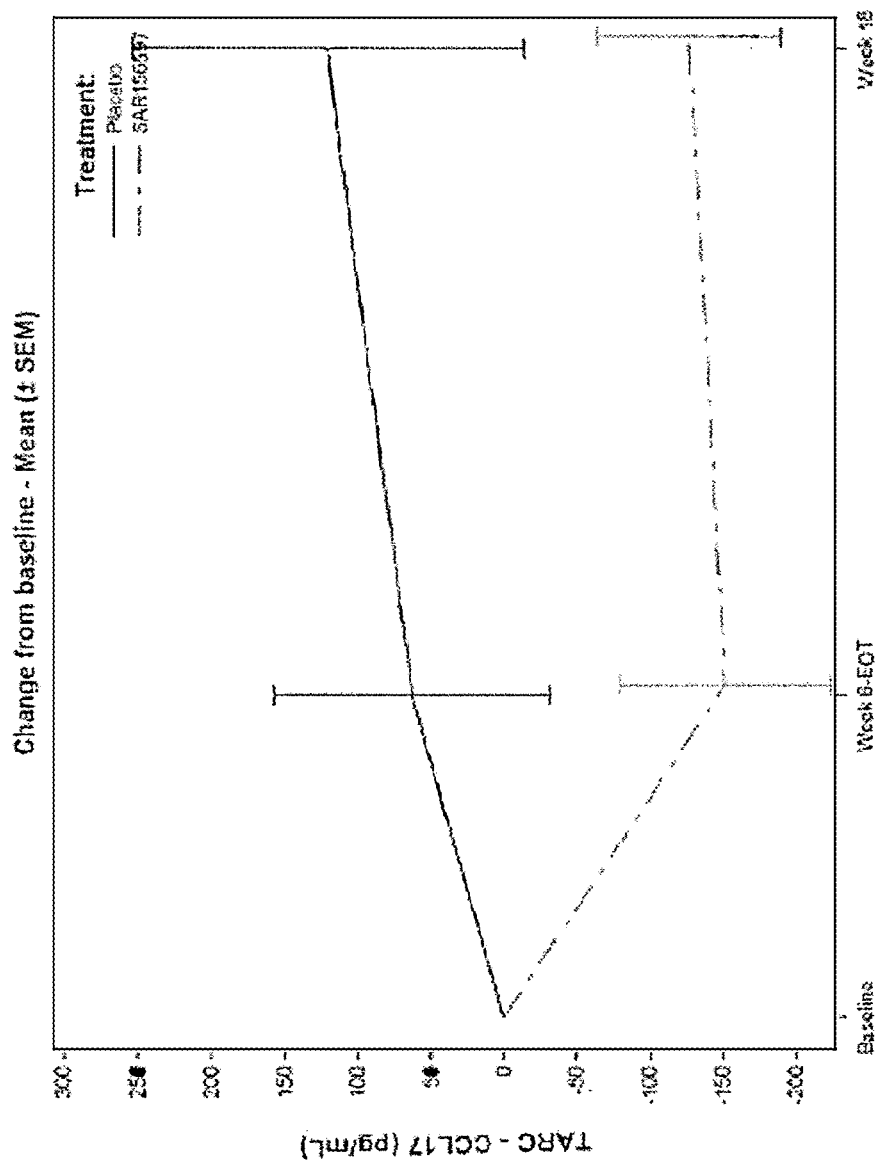
FIG. 3 shows persistent reduction in TARC/CCL17 expression in the blood of human subjects 18 weeks following the first administration of SAR156597. The graph shows the average amount of TARC/CCL17 versus time in the blood of patients administered 50 mg, 100 mg, or 200 mg SAR156597 SC once weekly.

There was a trend of reduced TARC (CCL-17) expression in the blood with increasing doses of SAR156597 (FIG. 2). Reduced TARC expression persisted post-EOT (FIG. 3).

Example 3: Analyses of Safety Data

A safety evaluation was based upon the review of the individual values (clinically significant abnormalities), descriptive statistics (summary tables, graphics). All the safety analyses were performed using the safety population.

For all safety data, the observation period were divided into 3 phases:

The pre-treatment phase, defined as the time between when the patients give informed consent and the first dose of IMP administration.

The on-treatment phase, defined as the time from the first dose of IMP administration up to the Week 18 visit (included).

The post-treatment phase, defined as the time after the Week 18 visit (excluded).

Adverse events were coded according to the Medical Dictionary for Regulatory Activities (MedDRA) using version 16.1.

For clinical laboratory, vital signs, and ECG parameters, and the potentially clinically significant abnormalities (PCSAs) were analyzed using the PCSA list shown in Table 2.

TABLE 2

Criteria for potentially clinically significant abnormalities (PCSAs)

| Parameter | PCSA | Comments |
|---|---|---|
| ALT and Total Bilirubin | ALT > 3 ULN and TBILI > 2 ULN | Concept paper on DILI - FDA draft Guidance October 2007. Internal DILI WG October 2008. To be counted within a same treatment phase, whatever the interval between measurement. |
| CPK | >3 ULN<br>>10 ULN | FDA February 2005. Am J Cardiol April 2006. Categories are cumulative. First row is mandatory. Rows following one mentioning zero can be deleted. |
| Creatinine | ≥150 μmol/L (Adults)<br>≥30% change from baseline<br>≥100% change from baseline | Benichou C., 1994. |
| Creatinine Clearance (Cokcroft's formula) | <30 ml/min (severe renal impairment)<br>≥30-<50 ml/min (moderate renal impairment)<br>≥50-≤80 ml/min (mild renal impairment) | Use is optional. FDA criteria May 1998. |
| Uric Acid<br>Hyperuricemia<br>Hypouricemia | >408 μmol/L<br><120 μmol/L | Harrison- Principles of internal Medicine 17$^{th}$ Ed., 2008. |
| Blood Urea Nitrogen | ≥17 mmol/L | |
| Chloride | <80 mmol/L<br>>115 mmol/L | |

TABLE 2-continued

Criteria for potentially clinically significant abnormalities (PCSAs)

| Parameter | PCSA | Comments |
|---|---|---|
| Sodium | ≤129 mmol/L | |
| | ≥160 mmol/L | |
| Potassium | <3 mmol/L | FDA February 2005. |
| | ≥5.5 mmol/L | |
| Total Cholesterol | ≥7.74 mmol/L | Threshold for therapeutic intervention. |
| Triglycerides | ≥4.6 mmol/L | Threshold for therapeutic intervention. |
| Lipasemia | ≥3 ULN | |
| Amylasemia | ≥3 ULN | |
| Glucose | | |
| Hypoglycaemia | ≤3.9 mmol/L and <LLN | ADA May 2005. |
| Hyperglycaemia | ≥11.1 mmol/L (unfasted); ≥7 mmol/L (fasted) | ADA January 2008. |
| HbA1c | >8% | |
| Albumin | ≤25 g/L | |
| CRP | >2 ULN or >10 mg/L (if ULN not provided) | FDA September 2005. |
| Hematology | | |
| WBC | <3.0 Giga/L (Non-Black); <2.0 Giga/L (Black) | Increase in WBC: not relevant. To be interpreted only if no differential count available. |
| | ≥16.0 Giga/L | |
| Lymphocytes | >4.0 Giga/L | |
| Neutrophils | <1.5 Giga/L (Non-Black); <1.0 Giga/L (Black) | International Consensus meeting on drug-induced blood cytopenias, 1991. FDA criteria. |
| Monocytes | >0.7 Giga/L | |
| Basophils | >0.1 Giga/L | |
| Eosinophils | >0.5 Giga/L or >ULN (if ULN ≥ 0.5 Giga/L) | Harrison- Principles of internal Medicine 17$^{th}$ Ed., 2008. |
| Hemoglobin | ≤115 g/L (Male); ≤95 g/L (Female) | Criteria based upon decrease from baseline are more relevant than based on absolute value. Other categories for decrease from baseline can be used (≥30 g/L, ≥40 g/L, ≥50 g/L). |
| | ≥185 g/L (Male); ≥165 g/L (Female) | |
| | Decrease from Baseline ≥20 g/L | |
| Hematocrit | ≤0.37 v/v (Male); ≤0.32 v/v (Female) | |
| | ≥0.55 v/v (Male); ≥0.5 v/v (Female) | |
| RBC | ≥6 Tera/L | Unless specifically required for particular drug development, the analysis is redundant with that of Hb. Otherwise, consider FDA criteria. |
| Platelets | <100 Giga/L | International Consensus meeting on drug-induced blood cytopenias, 1991. |
| | ≥700 Giga/L | |
| Urinalysis | | |
| pH | ≤4.6 | |
| | ≥8 | |
| Vital signs | | |
| HR | ≤50 bpm and decrease from baseline ≥20 bpm | To be applied for all positions (including missing) except STANDING. |
| | ≥120 bpm and increase from baseline ≥20 bpm | |
| SBP | ≤95 mmHg and decrease from baseline ≥20 mmHg | To be applied for all positions (including missing) except STANDING. |
| | ≥160 mmHg and increase from baseline ≥20 mmHg | |
| DBP | ≤45 mmHg and decrease from baseline ≥10 mmHg | To be applied for all positions (including missing) except STANDING. |
| | ≥110 mmHg and increase from baseline ≥10 mmHg | |
| Orthostatic Hypotension | | |
| Orthostatic SDB | ≤−20 mmHg | |
| Orthostatic DBP | ≤−10 mmHg | |
| Weight | ≥5% increase from baseline | FDA February 2007. |
| | ≥5% decrease from baseline | |
| ECG | | Ref.: CPMP 1997 guideline. |
| HR | ≤50 bpm and decrease from baseline ≥20 bpm | |
| | ≥120 bpm and increase from baseline ≥20 bpm | |
| PR | ≥220 ms and increase from baseline ≥20 ms | |
| QRS | ≥120 ms | |

TABLE 2-continued

Criteria for potentially clinically significant abnormalities (PCSAs)

| Parameter | PCSA | Comments |
|---|---|---|
| QTc<br>Borderline<br>Prolonged*<br>Additional | Absolute values (ms)<br>Borderline: 431-450 ms (Male); 451-470 ms (Female)<br>Prolonged: >450 ms (Male); >470 ms (Female)<br>≥500 ms<br>Increase from baseline<br>Borderline: Increase from baseline 30-60 ms<br>Prolonged: Increase from baseline >60 ms | To be applied to any kind of QT correction formula. |

*QTc prolonged and ΔQTc > 60 ms are the PCSA to be identified in individual subjects/patients listings.

Adverse Events

The adverse events (AEs) were classified into predefined standard categories according to chronological criteria:

Pre-treatment adverse events: AEs that occurred or worsened during the pre-treatment phase;

Treatment-emergent adverse events (TEAEs): AEs that occurred or worsened during the on-treatment phase;

Post-treatment adverse events: AEs that occurred or worsened during the post-treatment phase.

TEAEs were assigned to the IMP received at the time of the AE onset.

The numbers and percentages of patients with at least 1 TEAE, severe TEAE, serious TEAE, TEAE leading to death, and TEAE leading to permanent treatment discontinuation, were summarized by treatment group.

All TEAEs were summarized and listed by primary system organ class (SOC) and preferred term (PT). In addition, all AEs were listed, sorted by patient and onset date and time.

Clinical Laboratory Evaluations

Biochemistry and Hematology

The baseline value in this study was the value collected during Day 1 predose assessments.

For parameters with laboratory ranges and/or abnormality criteria (PCSAs), an "on-treatment" analysis was performed using all postbaseline assessments done during the on-treatment phase, including rechecked values.

Supplementary Tests for Vasculitis, Serology, and Urinalysis

All individual data were listed by treatment group, patient, and visit.

Weight and Body Mass Index:

The body weight was analyzed as the raw parameter value and the percent change from baseline. Individual body mass index was analyzed as raw value. The baseline values were the predose values collected on the Day 1. For all parameters, an "on-treatment" analysis was performed using all postbaseline values collected during the on-treatment phase, including all rechecked values.

Vital Signs:

Heart Rate and Blood Pressures.

Heart rate and blood pressure (systolic and diastolic blood pressure) were analyzed as raw parameter value (for supine and standing position available), the change from baseline (for supine position only), and as orthostatic parameter (standing-supine parameter values). The baseline values were the predose values collected on Day 1. For all parameters, an "on-treatment" analysis was performed using all postbaseline values collected during the on-treatment phase, including all unplanned and rechecked values.

Body Temperature:

The body temperature was analyzed as raw parameter value and change from baseline. The baseline values were the predose values collected on the Day 1.

Electrocardiogram:

Heart rate, PR-, QRS-, QT-, and corrected QT-interval (QTc) were analyzed as the raw parameter value and the change from baseline. The baseline values were the predose values collected on Day 1. For all parameters, an "on-treatment" analysis was performed using all postbaseline values collected during the on-treatment phase, including all rechecked values.

Other Related Safety Parameters (Local Tolerability at IMP Injection Site):

Erythema size and edema size were summarized in descriptive statistics by parameter, treatment group, and time-point. The numbers (%) of patients with the most extreme qualitative assessment of present pain intensity, erythema, edema, itch, papule, vesiculation, and pustule grades were summarized over the entire study by treatment group.

Extent of Exposure

Most patients received all 7 IMP injections in each treatment group. One patient in each SAR156597 dose group did not receive all 7 doses of study drug. One patient in each of the SAR156597 50 mg and 200 mg dose groups had dose interruptions related to evaluations for increased hsCRP and 1 patient in the SAR156597 100 mg dose group discontinued the study treatment due to a SAE of tuberculosis Adverse Events Overall, the number of treatment-emergent adverse events (TEAEs) was balanced across the treatment groups. Most TEAEs were mild or moderate in intensity and only 3 events were reported as severe: 1 event of ear infection in the placebo dose group, 1 event of femur fracture in the SAR156597 50 mg dose group, and 1 event of IPF in the SAR156597 200 mg dose group. Three patients experienced at least 1 serious adverse event (SAE): 1 patient in each of the SAR156597 treatment groups (Table 3).

TABLE 3

Overview of adverse event profile: treatment-emergent adverse events - Safety population

| n(%) | Placebo (N = 6) | SAR156597 50 mg (N = 6) | SAR156597 100 mg (N = 6) | SAR156597 200 mg (N = 6) |
|---|---|---|---|---|
| Subjects with any TEAE | 5 (83.3%) | 6 (100%) | 6 (100%) | 5 (83.3%) |
| Subjects with any severe TEAE | 1 (16.7%) | 1 (16.7%) | 0 | 1 (16.7%) |
| Subjects with any treatment emergent SAE | 0 | 1 (16.7%) | 1 (16.7%) | 1 (16.7%) |
| Subjects with any TEAE leading to death | 0 | 0 | 0 | 0 |
| Subjects with any TEAE leading to permanent treatment discontinuation | 0 | 0 | 1 (16.7%) | 0 |

TEAE: Treatment emergent adverse event,
SAE: Serious adverse event
N = Number of patients treated within each group,
n(%) = number and % of patients with at least one TEAE in each category
Note:
An adverse event is considered as treatment emergent if it occurred from the time of the first investigational medicinal product (IMP) administration up to the Week 18 visit (included)

The most commonly reported AEs were infections, the frequency of which were comparable among the treatment groups (3 of 6 patients in each of the placebo, SAR156597 50 mg and SAR156597 100 mg dose groups; 2 of 6 patients in the SAR156597 200 mg dose group) (Table 4). Four cases of accidental falls were reported as TEAEs. One event of fall that was reported as serious in the SAR156597 50 mg dose group subsequently resulted in an SAE of femur fracture, and 3 other cases reported in the SAR156597 200 mg dose group were mild in intensity.

TABLE 4

Number (%) of patients with at least 1 TEAE by primary SOC and PT - Safety population

| Primary system organ class Preferred term [n (%)] | Placebo (N = 6) | SAR156597 50 mg (N = 6) | SAR156597 100 mg (N = 6) | SAR156597 200 mg (N = 6) |
|---|---|---|---|---|
| Any class | 5 (83.3%) | 6 (100%) | 6 (100%) | 5 (83.3%) |
| Infections and infestations | 3 (50.0%) | 3 (50.0%) | 2 (33.3%) | 3 (50.0%) |
| Bronchitis | 0 | 0 | 0 | 1 (16.7%) |
| Conjunctivitis infective | 0 | 0 | 0 | 1 (16.7%) |
| Localised infection | 0 | 0 | 0 | 1 (16.7%) |
| Pneumonia bacterial | 0 | 0 | 0 | 1 (16.7%) |
| Ear infection | 1 (16.7%) | 0 | 0 | 0 |
| Epididymal infection | 0 | 1 (16.7%) | 0 | 0 |
| Nasopharyngitis | 1 (16.7%) | 1 (16.7%) | 1 (16.7%) | 0 |
| Tuberculosis | 0 | 0 | 1 (16.7%) | 0 |
| Urinary tract infection | 0 | 1 (16.7%) | 0 | 0 |
| Viral upper respiratory tract infection | 1 (16.7%) | 0 | 0 | 0 |
| Metabolism and nutrition disorders | 0 | 0 | 0 | 1 (16.7%) |
| Hypoglycaemia | 0 | 0 | 0 | 1 (16.7%) |
| Psychiatric disorders | 0 | 1 (16.7%) | 0 | 0 |
| Depression | 0 | 1 (16.7%) | 0 | 0 |
| Nervous system disorders | 2 (33.3%) | 0 | 1 (16.7%) | 0 |
| Dizziness | 1 (16.7%) | 0 | 0 | 0 |
| Headache | 2 (33.3%) | 0 | 0 | 0 |
| Somnolence | 0 | 0 | 1 (16.7%) | 0 |
| Tension headache | 1 (16.7%) | 0 | 0 | 0 |
| Cardiac disorders | 0 | 1 (16.7%) | 0 | 0 |
| Bundle branch block right | 0 | 1 (16.7%) | 0 | 0 |
| Respiratory, thoracic and mediastinal disorders | 0 | 0 | 3 (50.0%) | 2 (33.3%) |
| Cough | 0 | 0 | 2 (33.3%) | 1 (16.7%) |
| Idiopathic pulmonary fibrosis | 0 | 0 | 0 | 1 (16.7%) |
| Bronchitis chronic | 0 | 0 | 1 (16.7%) | 0 |
| Gastrointestinal disorders | 0 | 2 (33.3%) | 1 (16.7%) | 1 (16.7%) |
| Vomiting | 0 | 0 | 0 | 1 (16.7%) |
| Abdominal pain lower | 0 | 1 (16.7%) | 0 | 0 |
| Dry mouth | 0 | 0 | 1 (16.7%) | 0 |
| Nausea | 0 | 1 (16.7%) | 0 | 0 |
| Skin and subcutaneous tissue disorders | 0 | 2 (33.3%) | 2 (33.3%) | 3 (50.0%) |
| Diabetic foot | 0 | 0 | 0 | 1 (16.7%) |
| Hyperhidrosis | 0 | 0 | 0 | 1 (16.7%) |
| Macule | 0 | 1 (16.7%) | 0 | 1 (16.7%) |

TABLE 4-continued

Number (%) of patients with at least 1 TEAE
by primary SOC and PT - Safety population

| Primary system organ class<br>Preferred term [n (%)] | Placebo<br>(N = 6) | SAR156597 | | |
| --- | --- | --- | --- | --- |
| | | 50 mg<br>(N = 6) | 100 mg<br>(N = 6) | 200 mg<br>(N = 6) |
| Nail dystrophy | 0 | 0 | 0 | 1 (16.7%) |
| Blister | 0 | 0 | 1 (16.7%) | 0 |
| Lentigo | 0 | 1 (16.7%) | 0 | 0 |
| Papule | 0 | 1 (16.7%) | 0 | 0 |
| Skin fissures | 0 | 0 | 1 (16.7%) | 0 |
| Musculoskeletal and connective tissue disorders | 1 (16.7%) | 2 (33.3%) | 1 (16.7%) | 1 (16.7%) |
| Joint swelling | 0 | 0 | 0 | 1 (16.7%) |
| Back pain | 1 (16.7%) | 1 (16.7%) | 0 | 0 |
| Muscle spasms | 0 | 1 (16.7%) | 0 | 0 |
| Musculoskeletal stiffness | 0 | 0 | 1 (16.7%) | 0 |
| Renal and urinary disorders | 0 | 0 | 1 (16.7%) | 0 |
| Cystitis noninfective | 0 | 0 | 1 (16.7%) | 0 |
| General disorders and administration site conditions | 0 | 2 (33.3%) | 1 (16.7%) | 1 (16.7%) |
| Fatigue | 0 | 0 | 0 | 1 (16.7%) |
| Injection site erythema | 0 | 2 (33.3%) | 0 | 0 |
| Injection site pain | 0 | 0 | 1 (16.7%) | 0 |
| Injection site pruritus | 0 | 1 (16.7%) | 0 | 0 |
| Investigations | 0 | 1 (16.7%) | 0 | 3 (50.0%) |
| C-reactive protein increased | 0 | 1 (16.7%) | 0 | 3 (50.0%) |
| Injury, poisoning and procedural complications | 0 | 1 (16.7%) | 1 (16.7%) | 3 (50.0%) |
| Fall | 0 | 1 (16.7%) | 0 | 3 (50.0%) |
| Chest injury | 0 | 0 | 0 | 1 (16.7%) |
| Contusion | 0 | 0 | 0 | 1 (16.7%) |
| Limb crushing injury | 0 | 0 | 0 | 1 (16.7%) |
| Traumatic haematoma | 0 | 0 | 0 | 1 (16.7%) |
| Anaemia postoperative | 0 | 1 (16.7%) | 0 | 0 |
| Femur fracture | 0 | 1 (16.7%) | 0 | 0 |
| Injury | 0 | 0 | 1 (16.7%) | 0 |
| Laceration | 0 | 0 | 1 (16.7%) | 0 |

TEAE: Treatment emergent adverse event,
SOC: System organ class,
PT: Preferred term MedDRA 16.1
N = Number of patients treated within each group,
n (%) = number and % of patients with at least one TEAE in each category
Note:
Table sorted by SOC internationally agreed order and decreasing frequency of PT in SAR156597 200 mg group.
Note:
An adverse event is considered as treatment emergent if it occurred from the time of the first investigational medicinal product (IMP) administration up to the Week 18 visit (included)

Three patients experienced at least 1 SAE (1 in each of the SAR156597 treatment groups): 1 patient with SAE of fall and femur fracture in the SAR156597 50 mg dose group, 1 patient with SAE of tuberculosis in the SAR156597 100 mg dose group, and 1 patient with SAE of pneumonia bacterial and worsening IPF in the SAR156597 200 mg dose group. One patient discontinued the study treatment in the SAR156597 100 mg dose group due to a treatment-emergent SAE of tuberculosis.

Adverse Events of Special Interest (AESIs):

the suspicion of vasculitis, either based on sustained elevations (at least for 72 hours) in hsCRP that were >10 mg/L and >2× of baseline values or other clinical findings, was an AESI in this study. There were 3 cases of increased C-reactive protein reported in this study.

In these cases of elevated hsCRP that were reported as initial suspicion for potential vasculitis, none were confirmed to be vasculitis and most of these hsCRP increases were either in a time frame when infections also occurred (1 AESI triggered by hsCRP was associated with epididymal infection, 1 event associated with bacterial pneumonia, and 1 event with infective conjunctivitis) or considered by the Investigator as not clinically significant.

In the SAR156597 200 mg dose group, 1 patient had an initial report of splinter hemorrhage that was suspected by the Investigator to potentially be related to vasculitis. Upon further evaluations, this event was subsequently diagnosed as nail dystrophy and the suspicion of vasculitis was eventually disregarded.

Hematologic Parameters:

No significant changes in the hematology parameters were detected, except a few more patients in the SAR156597 treatment groups had PCSAs of more than 0.1 Giga/L basophil counts compared to the placebo groups Biochemistry Parameters:

One patient in each of the 3 SAR156597 treatment groups had transient elevation of hsCRP during this study.

Vital Signs:

The number of patients with orthostatic SBP and orthostatic DBP were higher in the SAR156597 treatment groups compared to placebo group.

Electrocardiograms:

The number of patients with QTcB prolongations was higher in the treatment groups compared to the placebo group. There were 4 patients (1 patient in the SAR156597 50 mg group, 2 patients in the SAR156597 100 mg group, and 1 patient in the SAR156597 200 mg group) who had QTcB prolongations during this study.

Injection Site Tolerability:

There were few local injection site reactions reported and most of the events were mild in severity.

Individual Clinically Relevant Abnormalities:

None of the vital signs that met the criteria for PCSA was associated with any clinically relevant manifestations, including the 4 cases of orthostatic SBP and 5 cases of orthostatic DBP, which all had other identifiable, potential contributing factors. None of the ECG results that met the criteria for PCSA was associated with any clinically relevant manifestations that required corrective treatment.

Safety Conclusions

All patients completed the 6-week treatment period with the exception of 1 patient in the SAR156597 100 mg SC weekly dose group who had to be discontinued from study treatment after the administrations of 3 doses of study drug due to an SAE of tuberculosis.

The number of patients with at least 1 TEAE was comparable among the treatment groups (5 of 6 patients in the placebo and 200 mg groups, 6 of 6 patients in the 50 mg and 100 mg groups), most TEAEs were mild to moderate in intensity. The most common reported TEAE was infections, which was balanced among the treatment groups (3 of 6 patients in the placebo, 50 mg, and 200 mg groups, 2 of 6 patients in 100 mg group).

Serious adverse event (SAE) was reported in 3 patients, 1 in each of the 3 SAR156597 dose groups (1 patient with SAEs of fall and femur fracture in the 50 mg dose group, 1 patient with SAE of tuberculosis in the 100 mg dose group, and 1 patient with SAE of pneumonia bacterial in the 200 mg dose group).

There was no death reported at any time of the study period.

None of the PCSAs from the hematology and biochemistry laboratory results, vital signs, and ECG were associated with any clinical manifestations. All patients with transient elevations of hsCRP were either associated with clinical events, such as infections, or were judged to be not clinically relevant by the Investigators. There were no confirmed cases of vasculitis in this study.

Overall, SAR156597 administered SC, weekly for 6 weeks at 3 different dose levels (50, 100, and 200 mg SC) was generally safe and well tolerated.

Example 4: Pharmacokinetics (PK) Assessments

Samples for PK analysis were collected pre-dose (within 2 hours before each dose administration) during Visits 2 to 8. Pharmacokinetics samples during Visits 9/early termination (ET), 11, and 14 were collected in the morning. Anti-SAR156597 antibodies (ADA) samples were collected at approximately the same times as the PK samples at Visits 2, 9/ET, 11, and 14. If, at Week 12, ADA related to immunogenicity were present, an additional follow-up visit occurred at a minimum of 6 months after the first dose to examine the elevated parameter.

SAR156597 plasma concentrations were determined using a validated enzyme linked immunosorbent assay (ELISA) method with a lower limit of quantification (LLOQ) of 0.05 pg/mL (DOH0850) under the responsibility of Bertin Pharma (L.E.M.M. [Laboratoire d'Etude du Metabolisme des Médicaments], DSV/iBiTec-S/SPI, CEA-Saclay, Gif sur Yvette Cedex, France). All raw data from the bioanalytical studies are stored at Bertin Pharma according to the procedures in use at the test site.

ADA in plasma was assayed using a validated ELISA method (DOH0851) under the responsibility of Disposition, Safety & Animal Research Operational Center of Montpellier (Biomarker and Biological Assays group), Sanofi. All samples were first evaluated using a screening assay. Samples found positive in the screening assay were then tested in a confirmatory assay. A titer was reported only for samples confirmed to be positive. All raw data from the bioanalytical studies are stored at sanofi-aventis, Montpellier, France, according to the procedures in use at the test site.

Pharmacokinetic parameters were estimated using the population PK (Bayesian) approach and are presented in Table 5.

TABLE 5

List of pharmacokinetic parameters for plasma SAR156597 and definitions

| Parameters | Definition/Calculation |
|---|---|
| $C_{max}$ | Maximum plasma concentration observed after $1^{st}$ and last dose |
| $t_{max}$ | First time to reach $C_{max}$ after $1^{st}$ and last dose |
| $AUC_{0-168}$ | Area under the plasma concentration versus time curve calculated using the trapezoidal method from time zero to 168 hours post dose after $1^{st}$ and last dose |
| $t_{1/2z}$ | Terminal half-life after last dose |

The Bayesian analysis was performed with the NON-MEM® computer program (version 7.1.2) running on a LINUX cluster of multi-processor computers.

A Bayesian Data Set was constructed using data of the 3 cohorts (doses 50, 100, and 200 mg). The NONMEM software (version 7.1.2) was used to analyze the data. The final population PK model obtained in POH0338 study (constructed using PK data from an earlier study) was applied to the Bayesian Data Set, with its parameter estimates as prior estimates for the assessment of individual parameters and concentration predictions. The estimation step was omitted using the option MAXEVAL=0 to compute the individual estimates based on the final population estimates of θ (fixed effect of the model, ie, PK parameters), w (inter-individual variability), and σ (intra-individual variability) obtained in the final population PK model.

Analyses of Pharmacokinetic Data

All the PK analyses were performed using the population PK approach. The following PK parameters were determined in this study:

Observed SAR156597 plasma trough concentrations ($C_{trough}$);

Individual predicted $C_{max}$, and predicted $AUC_{0-168h}$ after first and last dose; Individual predicted $t_{1/2z}$ after last dose.

Statistical Analysis

Assayed SAR156597 $C_{trough}$ concentrations and predicted $C_{max}$, $AUC_{0-168h}$, and $t_{1/2z}$ were summarized by descriptive statistics (arithmetic and geometric mean, median, SD, coefficient of variation [CV %], minimum, maximum, median, and the number of available observations) for each treatment group under the responsibility of Disposition, Safety & Animal Research, Sanofi. Other statistical analyses such as steady state assessment, dose effect on $t_{1/2z}$ and dose proportionality were performed under the responsibility of Biostatistics, Sanofi.

Prior to all statistical analyses, $C_{max}$, $AUC_{0-168h}$, and $t_{1/2z}$ were log-transformed.

The occurrence of steady state was assessed by fitting $C_{trough}$ values with a non-linear mixed effects model using the SAS NLMIXED procedure.

Dose effect for $t_{1/2z}$ was assessed with a linear fixed effect model.

Dose proportionality for $C_{max}$ and $AUC_{0-168h}$ was assessed using a power model.

Pharmacokinetic Data Handling and Data Quality Assurance:

The plasma drug concentration lower than the LLOQ of 0.05 pg/mL for SAR156597 was treated as zero in calculating the mean values. Means and their associated statistics were generated from unrounded numbers and may differ slightly from those values which would have been determined using rounded numbers. Once final PK analysis was performed, the PK parameters were transferred electronically to the Biostatistics Department for further statistical analysis. Concentrations and PK parameter values were rounded to 3 significant figures.

Pharmacokinetics Evaluation

Figure 4:
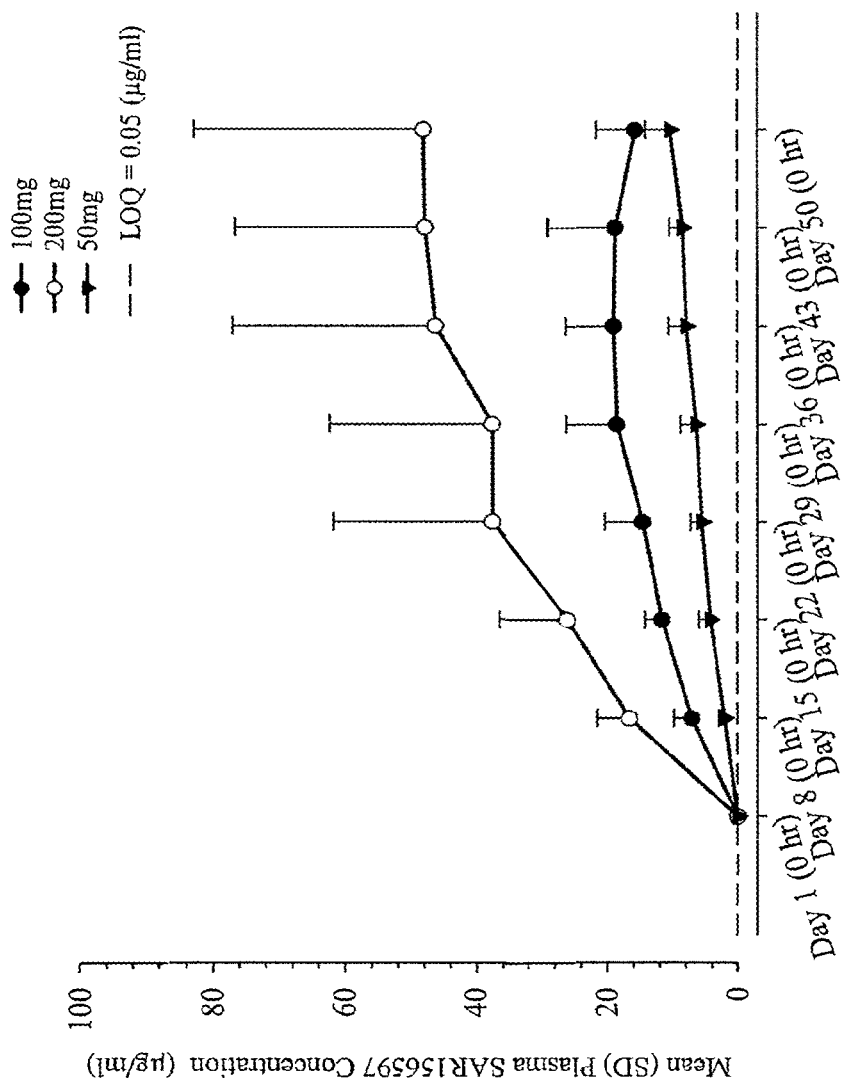
FIG. 4 shows SAR156597 trough concentrations over time by dose level (n=6, except n=5 at 100 mg).

Plasma Concentrations:

All 18 patients randomized to SAR156597 were exposed to SAR156597. No SAR156597 was detected in plasma from the 6 placebo patients. One patient at 100 mg was excluded from PK analysis due to insufficient number of doses received. SAR156597 trough concentrations are graphically presented in FIG. 4.

For 100 mg and 200 mg doses of SAR156597 given once a week, the median time to reach 90% of steady state was around Day 34. For 50 mg dose of SAR156597 given once a week, statistical analysis provides an unexpected median time to reach steady state around 101 days. The above time to steady state estimate in the 50 mg dose group may not be reliable, because of low plasma trough concentrations. Consequently, the non-linear mixed effects model apparently failed to properly assess the initial slope parameter for the 50 mg dose group, leading to an overestimated time to steady state at this dose level.

Besides, the Bayesian PK analysis predicted that the steady state for $AUC_{0-168ss}$ was reached at 89% for 50 mg dose group, 94.8% for 100 mg dose group, and 93.7% for 200 mg dose group after seventh dose of SAR156597 on Week 6.

Pharmacokinetic Parameters:

Descriptive statistics of PK parameters of SAR156597 obtained after single SC administration of SAR156597 on Week 1 are summarized in Table 6.

TABLE 6

SAR156597 plasma PK parameters after single dose (1st dose).

Mean ± SD [CV %] Plasma SAR156597

|  | 50 mg | 100 mg | 200 mg |
|---|---|---|---|
| N | 6 | 5 | 6 |
| $C_{max}$ (µg/ml) | 2.91 ± 0.493 [17%] | 7.56 ± 0.1.99 [26%] | 17.5 ± 4.93 [28%] |
| $t_{max}$[a] (hr) | 99.4 [81.3-123] | 95.8 [74.4-105] | 99.2 [79.6-139] |
| $AUC_{0-168}$ (µg · hr/ml) | 411 ± 63.2 [15%] | 1070 ± 275 [26%] | 2430 ± 626 [26%] |

[a]Median (min-max)

Descriptive statistics of PK parameters of SAR156597 obtained after weekly repeated SC administration of SAR156597 on Week 6 are summarized in Table 7.

TABLE 7

SAR156597 plasma PK parameters after 7 weekly doses (Week 6). Mean ± SD [CV %] Plasma SAR156597

|  | 50 mg | 100 mg | 200 mg |
|---|---|---|---|
| N | 6 | 5 | 6 |
| $C_{max}$ (µg/ml) | 10.2 ± 2.79 [27%] | 22.5 ± 7.42 [33%] | 55.0 ± 23.6 [43%] |
| $t_{max}{}^a$ (hr) | 56.7 [52.2-65.6] | 56.0 [47.8-56.7] | 58.6 [52.2-91.5] |
| $AUC_{0-168}$ (µg · hr/ml) | 1630 ± 468 [29%] | 3510 ± 1210 [34%] | 8670 ± 3920 [45%] |

$^a$Median (min-max)

SAR156597 $t_{1/2z}$ estimates with 90% CI are presented in Table 8. The $t_{1/2z}$ ranged between 260 hours (approximately 11 days) and 348 hours (approximately 15 days) with an unexpected significant dose effect on $t_{1/2z}$ (p=0.049).

TABLE 8

Point estimates of t½z with 90% confidence intervals.

| Parameter | Group | Estimate | 90% CI |
|---|---|---|---|
| $t_{1/2z}$ (h) | SAR156597 50 mg | 348.15 | (302.76 to 400.35) |
|  | SAR156597 100 mg | 260.63 | (223.64 to 303.73) |
|  | SAR156597 200 mg | 270.58 | (235.30 to 311.15) |

Dose proportionality assessment was performed on Week 1 and Week 6 and is presented in Tables 9 and 10, respectively.

TABLE 9

Point estimates with 90% confidence interval for r-fold increases on Week 1.

|  |  | Ratio | |
|---|---|---|---|
| Parameter | Dose ratio | Estimate | 90% CI |
| $C_{max}$ | (r) = 2 | 2.43 | (2.17 to 2.73) |
|  | (r) = 4 | 5.92 | (4.71 to 7.44) |
|  | Beta Estimate | 1.28 | (1.12 to 1.45) |
| $AUC_{0-168}$ | (r) = 2 | 2.41 | (2.17 to 2.69) |
|  | (r) = 4 | 5.83 | (4.69 to 7.24) |
|  | Beta Estimate | 1.27 | (1.12 to 1.43) |

$C_{max} = 0.02 \times dose^{1.28}$
$AUC_{0-168} = 2.86 \times dose^{1.27}$

TABLE 10

Point estimates with 90% confidence interval for r-fold increases on Week 6.

|  |  | Ratio | |
|---|---|---|---|
| Parameter | Dose ratio | Estimate | 90% CI |
| $C_{max}$ | (r) = 2 | 2.28 | (1.94 to 2.68) |
|  | (r) = 4 | 5.21 | (3.78 to 7.20) |
|  | Beta Estimate | 1.19 | (0.96 to 1.42) |
| $AUC_{0-168}$ | (r) = 2 | 2.27 | (1.92 to 2.69) |
|  | (r) = 4 | 5.17 | (3.68 to 7.25) |
|  | Beta Estimate | 1.18 | (0.94 to 1.43) |

$C_{max} = 0.09 \times dose^{1.19}$
$AUC_{0-168} = 14.95 \times dose^{1.18}$

On Week 1 and on Week 6, SAR156597 exposure increased slightly more than dose proportionally. A 4-fold increase in SAR156597 dose demonstrated a 5.21- to 5.92-fold increase in $C_{max}$ and a 5.17- to 5.83-fold increase in $AUC_{0-168}$.

Immunogenicity: ADA Determination in Plasma.

Summary of ADA results are described in Table 11.

TABLE 11

Summary of ADA results.

| ADA category | placebo | | 50 mg SC | | 100 mg SC | | 200 mg SC | | overall | |
|---|---|---|---|---|---|---|---|---|---|---|
|  | n | % | n | % | n | % | n | % | n | % |
| negative | 5 | 80 | 6 | 100 | 6 | 100 | 4 | 80 | 22 | 91.7 |
| positive | 1 | 20 | 0 | 0 | 0 | 0 | 1 | 20 | 2 | 8.3 |
| Pre-treatment reactivity | — | — | — | — | — | — | 1 | 20 | — | — |
| Treatment emergent | — | — | — | — | — | — | — | — | — | — |
| transient | — | — | — | — | — | — | — | — | — | — |
| persistent | — | — | — | — | — | — | — | — | — | — |
| All ADA subjects | 6 | — | 6 | — | 6 | — | 5* | — | 23 | — |

Two patients had ADA positive samples. One patient (Patient no. 152003002) in the SAR156597 200 mg treatment group exhibited ADA reactivity in the pretreatment sample on Day 1, but the ADA reactivity was negative in all samples up to Week 18. The second patient (Patient no. 484002003) was on placebo treatment and was ADA positive on Week 12 and on Week 18. Therefore, ADAs were considered to have no impact on SAR156597 PK parameters estimation.

For 1 patient (Patient no. 124003001) in the 200 mg treatment group, the post-treatment ADA analysis was not performed due to unavailability of the samples (samples not collected).

Pharmacokinetic Conclusions

All 17 patients randomized to SAR156597 were exposed to SAR156597.

No SAR156597 was detected in plasma from the 6 placebo patients.

Bayesian PK analysis predicted that 89% to 94.7% of steady state was reached after 7 doses of SAR156597 on Week 6.

The $t_{1/2z}$ ranged between 260 hours (approximately 11 days) and 348 hours (approximately 15 days) with unexpected significant dose effect on $t_{1/2z}$ (p=0.049).

On Week 1 and on Week 6, SAR156597 exposure increased slightly more than dose proportionally. A 4-fold increase in SAR156597 dose demonstrated a 5.21- to 5.92-fold increase in $C_{max}$ and a 5.17- to 5.83-fold increase in $AUC_{0-168}$.

No significant treatment-emergent ADA reactivity developed as a consequence of treatment with SAR156597.

Example 5: IL-13 is a Driver of Pulmonary Fibrosis in a FRA-2 Transgenic Mouse Model Interstitial lung disease (ILD) refers to a large group of more than 200 lung diseases affecting the interstitium. A significant subset of scleroderma patients show pulmonary manifestation with parenchymal lung involvement resulting in interstitial lung abnormalities and compromised pulmonary function. This fatal end-stage condition is characterized by interstitial pneumonia and scarring.

The AP-1 family of transcription factors regulates the expression of a number of target genes that control a variety of cellular functions. The AP-1 complex is composed of Jun and Fos proteins. Fos-Like Antigen 2, FRA-2, a member of the Fos family of proteins, participates in the AP-1 complex formation with a regulatory function.

Eferl et al. previously demonstrated that overexpression of FRA-2 in transgenic mice caused fibrosis in several organs but mainly affected pulmonary tissues and the skin (Eferl et al., 2008, Proc. Natl. Acad. Sci. 105(30): 10525-10530).

This example describes the characterization of a new line of transgenic mice overexpressing the Fra-2 gene. These mice showed fibrosis of the lungs during development starting at thirteen weeks. The development of fibrosis coincides with elevated levels of circulating and pulmonary Th2 cytokines.

Figure 19A:
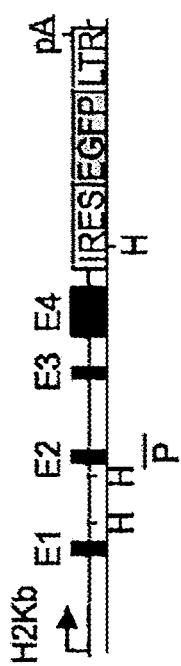
FIG. 19A shows the transgenic constructs for ectopic expression of Fra-2 in vivo as used in Eferl et al., 2008, Proc. Natl. Acad. Sci. 105(30): 10525-10530.

In the transgene produced by Eferl et al., an EGFP gene was engineered into the construct to enable visualization of the transgene expression. The full length FRA2 gene was driven by an H2kb promoter resulting in the ubiquitous expression of the transgene. The Eferl transgenic construct is shown in FIG. 19A and consists of an H2Kb promoter, the genomic Fra-2 locus, a reporter IRES-EGFP sequence, and a LTR sequence harboring a polyadenylation signal (pA). E1-E4 are Exons 1-4 of Fra-2; HindIII (H) restriction sites and probe location (P) used for Southern blot analysis are indicated.

Figure 19B:
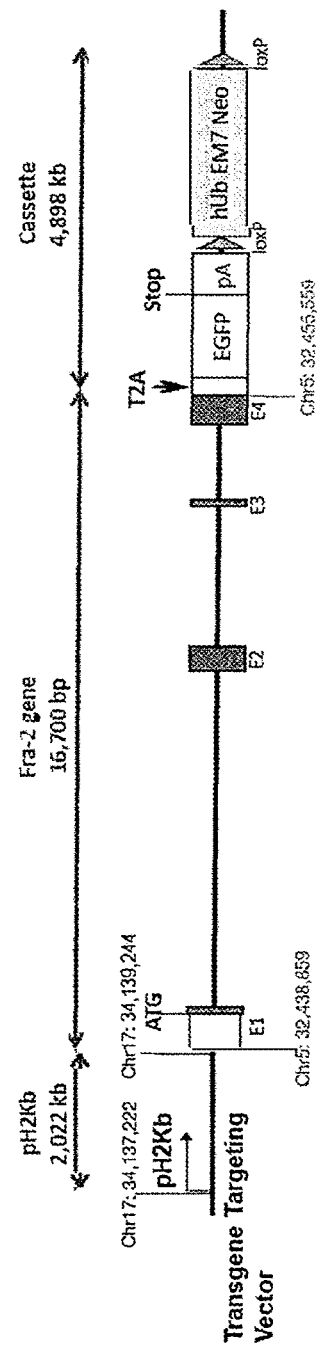
FIG. 19B shows the Fra-2 transgenic vector used herein, as described in Example 5.

By contrast, FIG. 19B shows a schematic of the transgenic vector used here, which contains a mouse H2Kb promoter driving mouse Fra-2 gene and a T2A-EGFP-polyA-loxP-hUBp-EM7-Neo-loxP cassette (4,898 bp). Four to eight copies of the transgene were randomly integrated into the host chromosome. Five founder transgenic lines over-expressing FRA2 were generated; three lines were triaged for further characterization based on transgene expression. The genomic coordinates of the fragments were as follows: H2Kb (H2-K1) promoter: Chr17: 34,137,222-34,139,244 (-) after Morello et al., 1986, EMBO J. 5(8): 1877-83; Fra-2 (Fosl2) gene (without stop): Chr5: 32,438,859-32,455,559.

In a preliminary observational study, impact of the transgene during development was studied at weeks 8, 14 and 16. There were no differences in body weight or mortality during this period between the wild type controls and the FRA2 mice. This observation was in contrast to observations of 50% mortality at week 16 by Eferl et al.

Figure 5C:
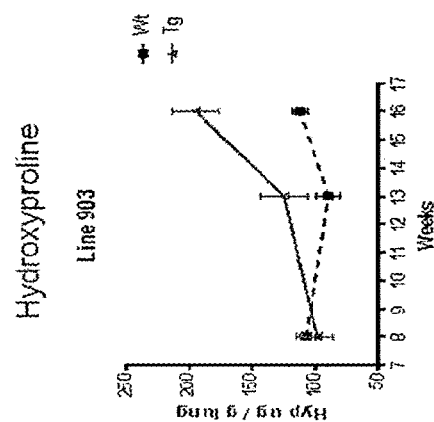
FIGS. 5A-5C shows fibrotic changes in the lungs of FRA-2 overexpressing transgenic mice over time. A. Increase in lung weights during development; B. increase in lung size at week 16; C. increase in hydroxyproline content in the lungs of Tg (FRA2) and Wt control mice.
Figure 5B:
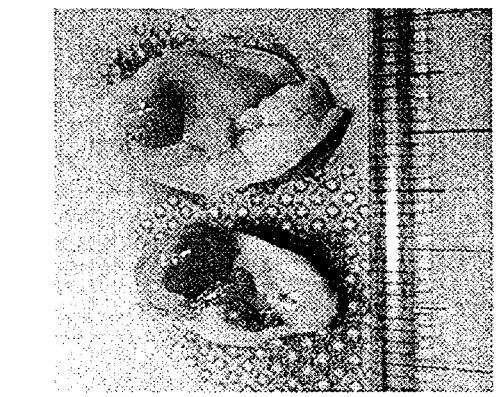
Figure 5A:
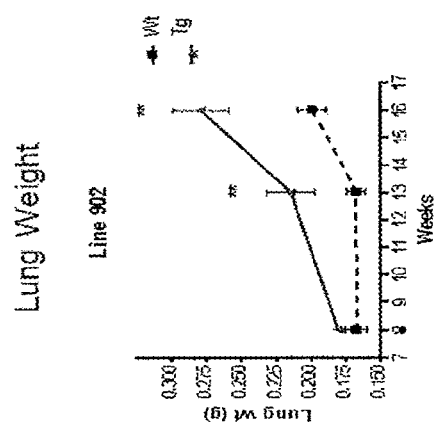

The FRA-2 over-expressing transgenic mice exhibited increasing lung weights with age accompanied by an increased deposition of collagen measured by hydroxyproline content (FIG. 5).

Figure 6:
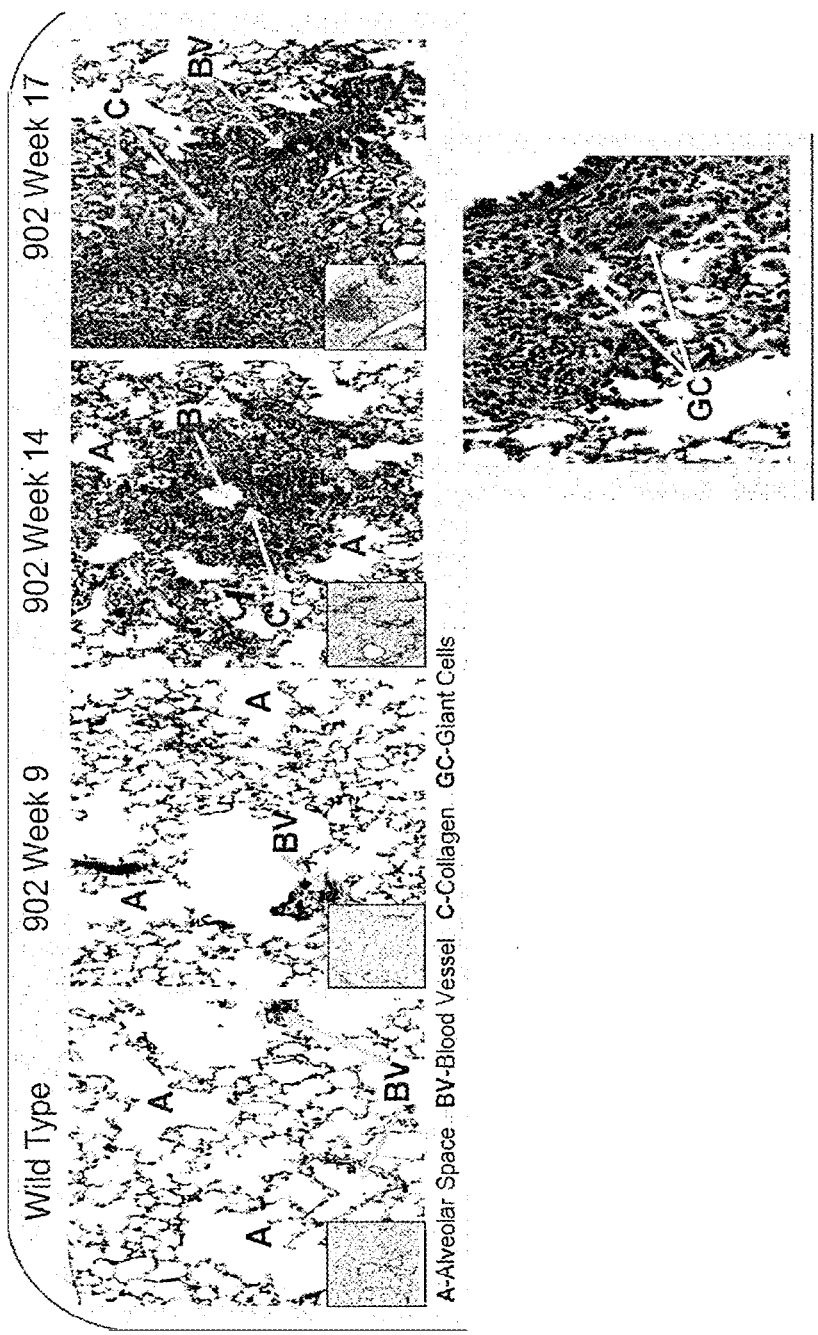
FIG. 6 shows images of lung samples of FRA-2 overexpressing mice at 9, 14, and 17 weeks.

In this model, there was an early inflammatory phase with an influx of inflammatory cells into the lungs (FIG. 6). Histological analysis also showed increased deposition of collagen with time in lung samples and was conducted as follows. Following euthanasia, the lungs were insufflated with fixative under a fixed pressure. The lungs were then removed and placed into fixative. After fixation was complete, the lungs were embedded into a 1% agar solution and were sliced transsagitally into 3 mm thick step sections. After processing, all sections were embedded into paraffin blocks. All paraffin blocks were microtomed at 4 µm and stained using Masson's Trichrome stain to demonstrate collagen deposition (blue) ad H&E stain to show overall morphology (FIG. 6).

Figure 7:
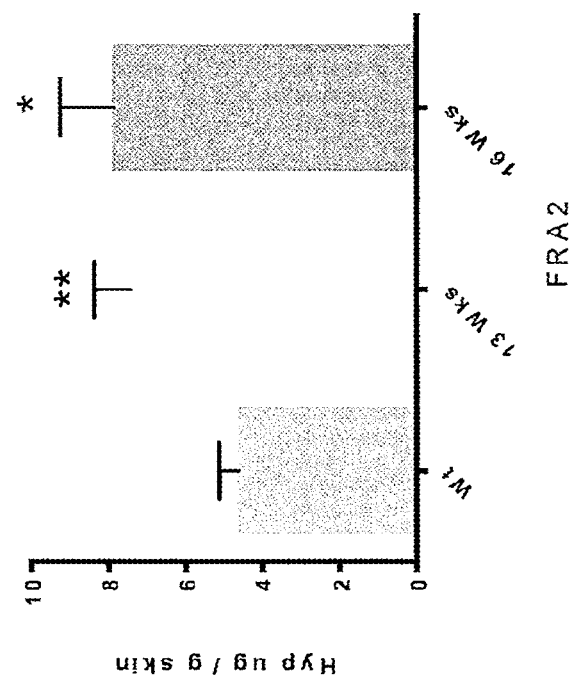
FIG. 7 shows collagen content, as measured by hydroxyproline) in the skin of FRA2 mice at 13 and 16 weeks compared to wild-type control.
Figure 8:
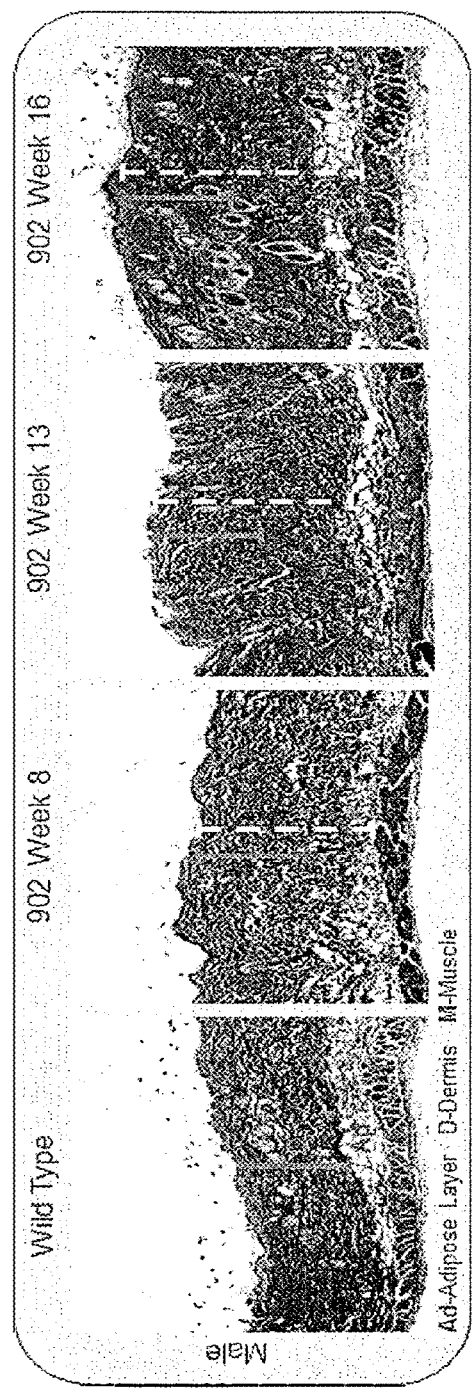
FIG. 8 shows the increased dermal thickness in samples from FRA2 mice at 8, 13, and 16 weeks compared to wild-type control.

Similarly, in the skin there was an increase in dermal thickness of FRA2 mice over time, paralleled by collagen deposition in the skin, compared to wild-type controls (FIGS. 7 and 8).

In this model, there was an early inflammatory phase with an influx of inflammatory cells into the lungs and an up-regulation of Th2 cytokines like IL-4 & IL-13. A late fibrotic phase follows where there is an up-regulation of fibrotic genes (ECM proteins & mediators) in the lungs and skin.

Figure 9:
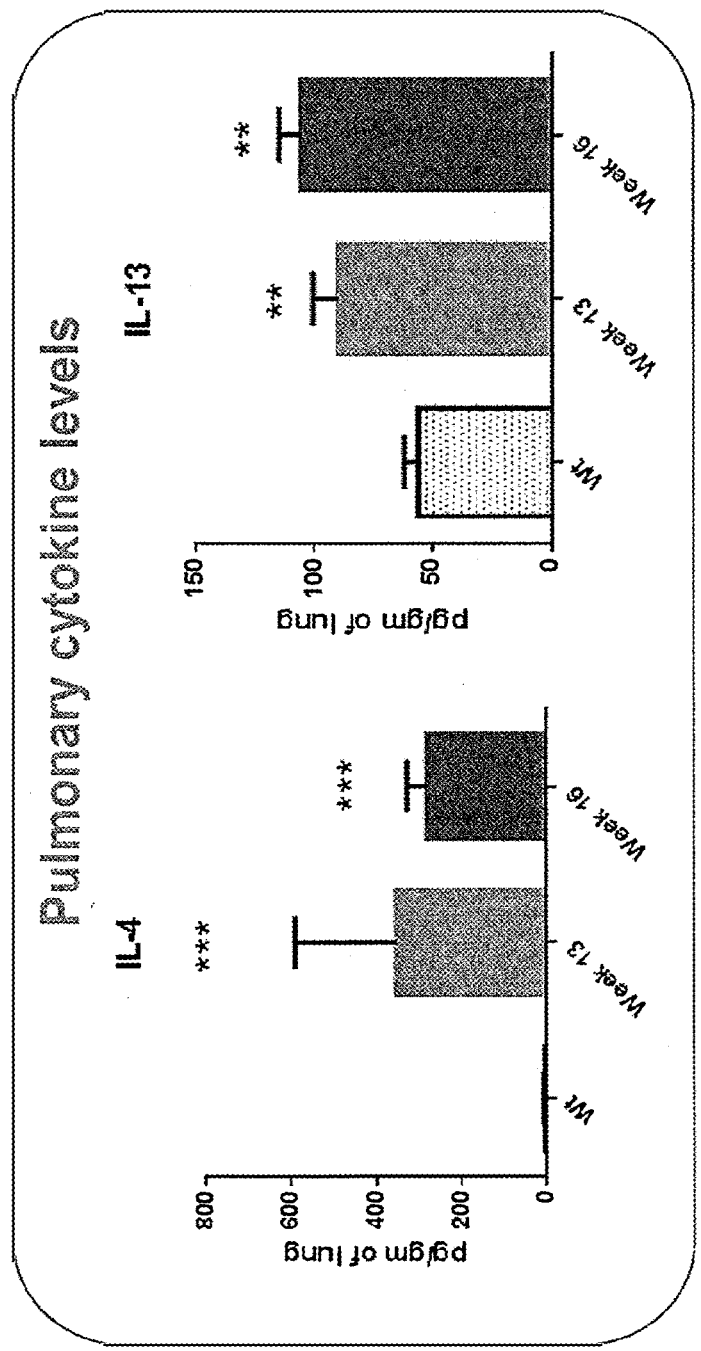
FIG. 9 shows a cytokine profile analysis of the developing and fibrosing lungs and skin.

A cytokine profile analysis of the developing and fibrosing lungs showed an increase in the Th2 cytokine profile (IL-4, IL-5 and IL-13) (FIG. 9). A significant increase in IL-4 and IL-13 levels were observed by week 13 of development, remaining elevated through week 17 which parallels the development of pulmonary fibrosis in these animals.

Figure 10:
FIG. 10 shows a gene expression analysis of the lungs and skin from FRA2 mice, showing an increase in key signatory fibrotic markers.

Gene expression analysis of the lungs and skin from FRA2 mice in a developmental gene regulation study showed an increase in key signatory fibrotic markers, including TGF-b pathway transcripts, IL-4, IL-13, STATE, profibrotic chemokines, and LOX (FIG. 10).

This developmental pulmonary fibrosis mouse model was used to study a role for IL-4 and IL-13 in fibrosis. First, a role for IL-13 in promoting fibrosis was evaluated using a validated surrogate mouse IL-13 antibody (since there is no cross reactivity of SAR156597 in rodents) with neutralizing activity in the FRA2 mouse model. Thirteen week old FRA2 mice were dosed with the surrogate mouse IL-13 antibody, at 10 mpk, administered by the ip route twice a week for 29 days. A rat IgG1 isotype at 10 mpk was dosed in parallel FRA2 mice as controls. Similarly, a third group of FRA2 mice received saline as a second control group. The below table shows the different treatment groups used in the study.

TABLE 12

Treatment groups used in the IL-13 antibody mouse study.

| Group | Genotype | Treatment | n |
|---|---|---|---|
| 1 | WT | Saline | 15 |
| 2 | WT | Isotype | 15 |
| 3 | FRA-2 Het | Saline | 16 |
| 4 | FRA-2 Het | Isotype | 16 |
| 5 | FRA-2 Het | Anti-IL-13 | 16 |

Figure 11:
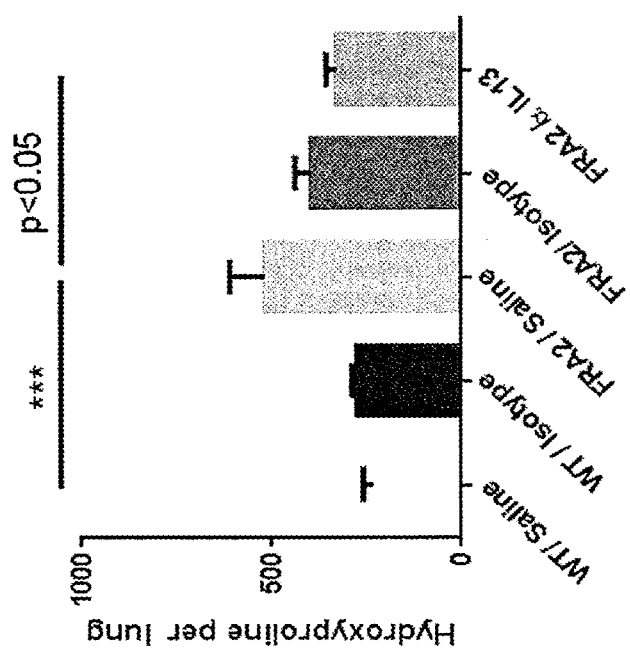
FIG. 11 shows hydroxyproline levels in IL-13 Ab treated FRA2 mouse lungs.

At the end of the study, the mice were euthanized and their lungs removed and processed to provide (1) lung homogenates for protein analysis, (2) RNA preparation, and (3) one lung lobe was tied off and insufflated, excised and fixed for histological analysis. The lung homogenates were used to quantitate the amount of collagen. As shown in FIG. 11, the hydroxyproline content of FRA2 mouse lungs was increased compared to the wt littermate controls. The hydroxyproline levels in the IL-13 Ab treated FRA2 mouse lungs was significantly decreased.

Figure 12:
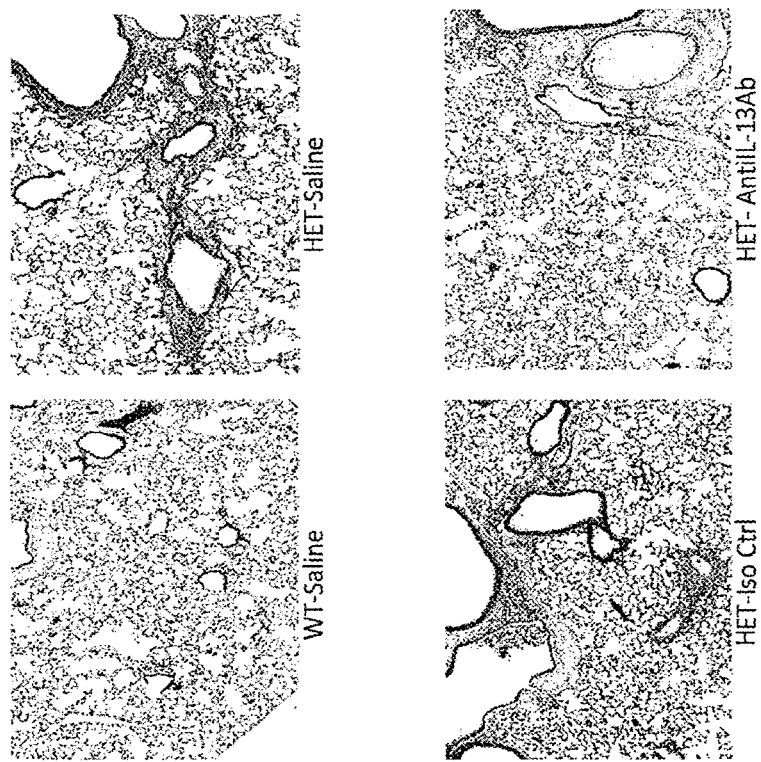
FIG. 12 shows histopathology analysis of FRA2 and littermate control lungs.
Figure 13:
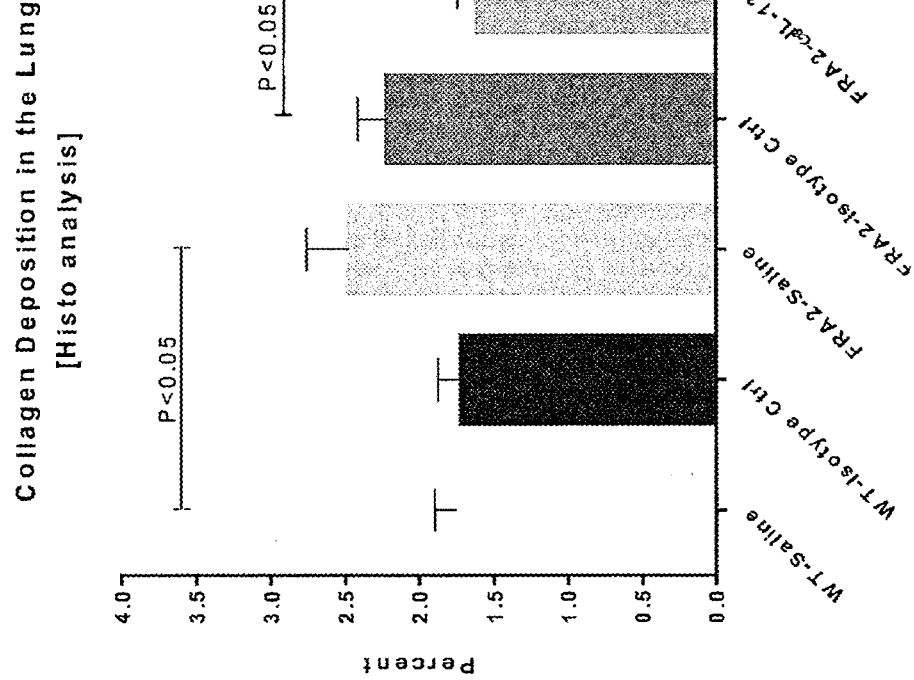
FIG. 13 shows the quantitation of the histopathology analysis of FRA2 and littermate control lungs shown in FIG. 12.

This observation was confirmed at the cellular level by histopathology analysis of the FRA2 and littermate control lungs (FIG. 12). Trichrome blue stained lung sections showed increased collagen deposits in FRA2 mouse control groups (saline and isotype control treated) compared to the corresponding wild type mice. A decrease in trichrome blue staining, reflective of reduced collagen content, was observed in the anti-IL-13 Ab treated mice lungs (quantitated in FIG. 13). These results clearly demonstrate the role of IL-13 in promoting pulmonary fibrosis via collagen deposition and the ability of a surrogate anti-IL-13 Ab to inhibit collagen deposition.

Figure 14:
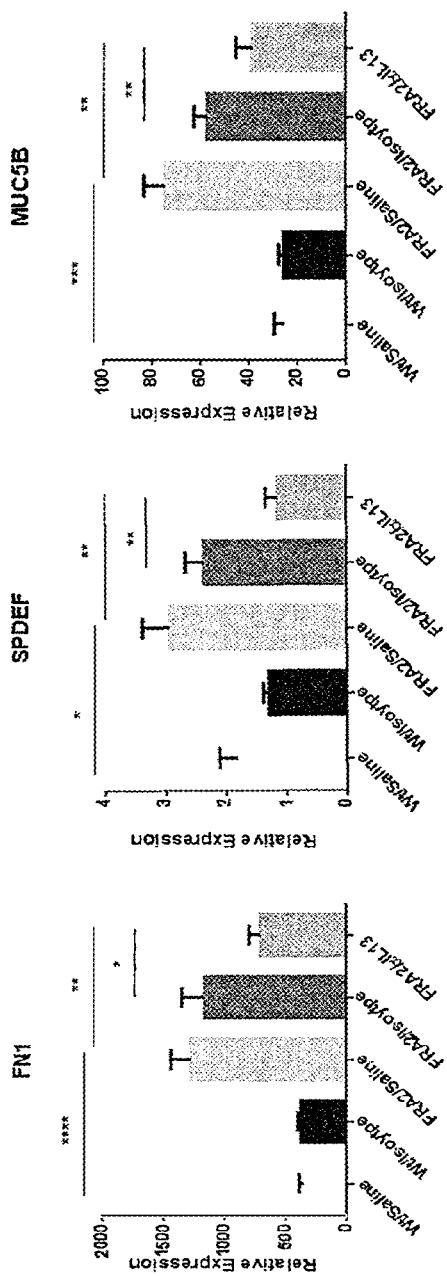
FIG. 14 shows transcript analysis by real-time PCR for IPF biomarkers FN1, SPDEF, and MUC5B.
Figure 15:
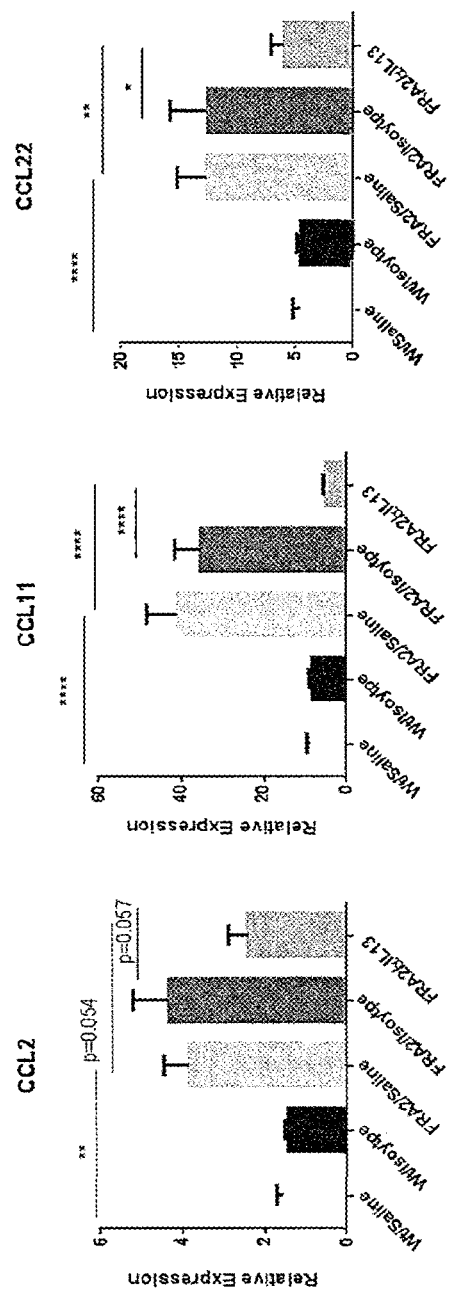
FIG. 15 shows transcript analysis by real-time PCR for profibrotic markers CCL2, CCL11, and CCL22.
Figure 16:
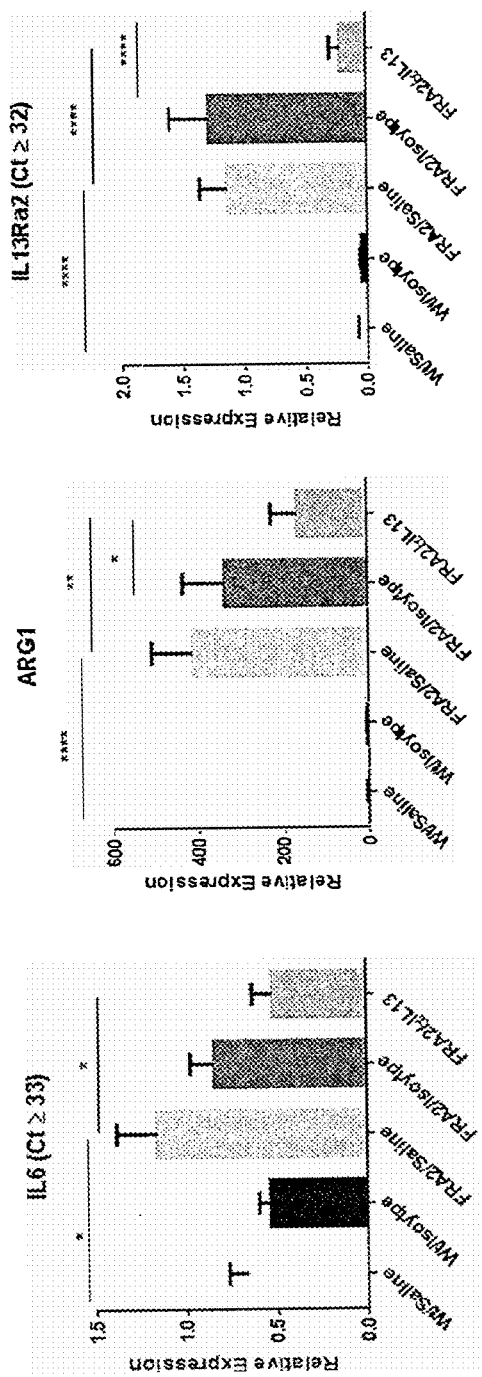
FIG. 16 shows transcript analysis by real-time PCR for IL-6, ARG1, and IL13Ra2.

Transcript analysis by real time PCR was used to follow the expression of a variety of fibrotic markers, profibrotic mediators and genes that are regulated by IL-13. Results for IPF biomarkers FN1, SPDEF, and MUC5B are shown in FIG. 14. Results for profibrotic markers CCL2 and CCL11 are shown in FIG. 15. Results for IL-6, ARG1, and IL13Ra2 are shown in FIG. 16.

Figure 17:
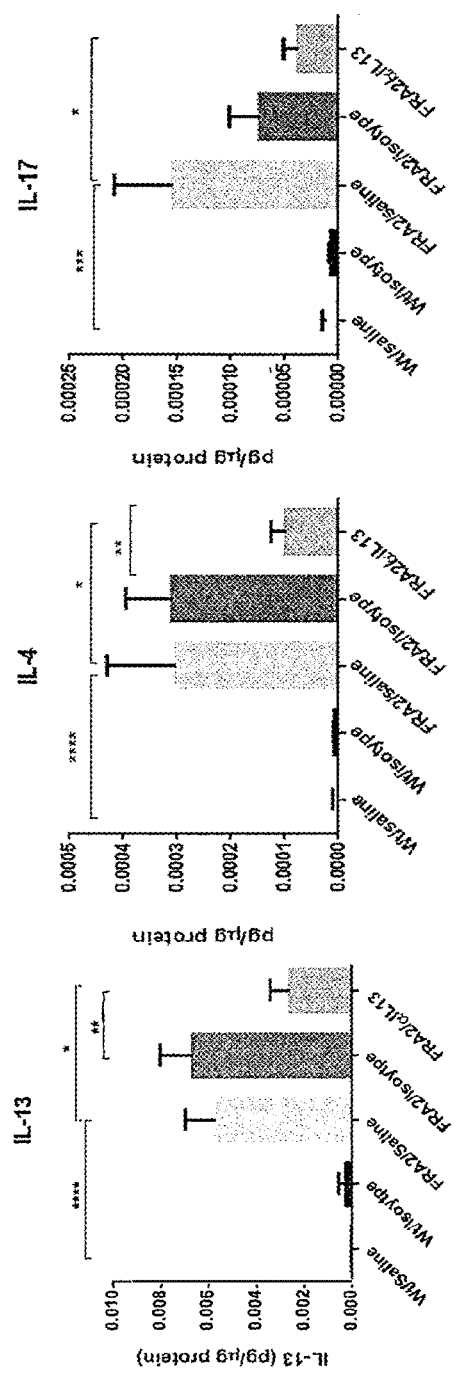
FIG. 17 shows IL-13, IL-4, and IL-17 protein expression levels in lung homogenates, as analyzed by ELISA.

IL-13-regulated protein expression was further studied in lung homogenates by ELISA. IL-13, IL-4 and IL-17 levels were increased in the FRA2 lung homogenates compared to wild type lungs and these cytokine levels were attenuated following anti-IL-13 Ab treatment (FIG. 17). Decreased IL-13 levels confirmed antibody loading in the lungs following the 4 wk treatment (FIG. 17).

Figure 18:
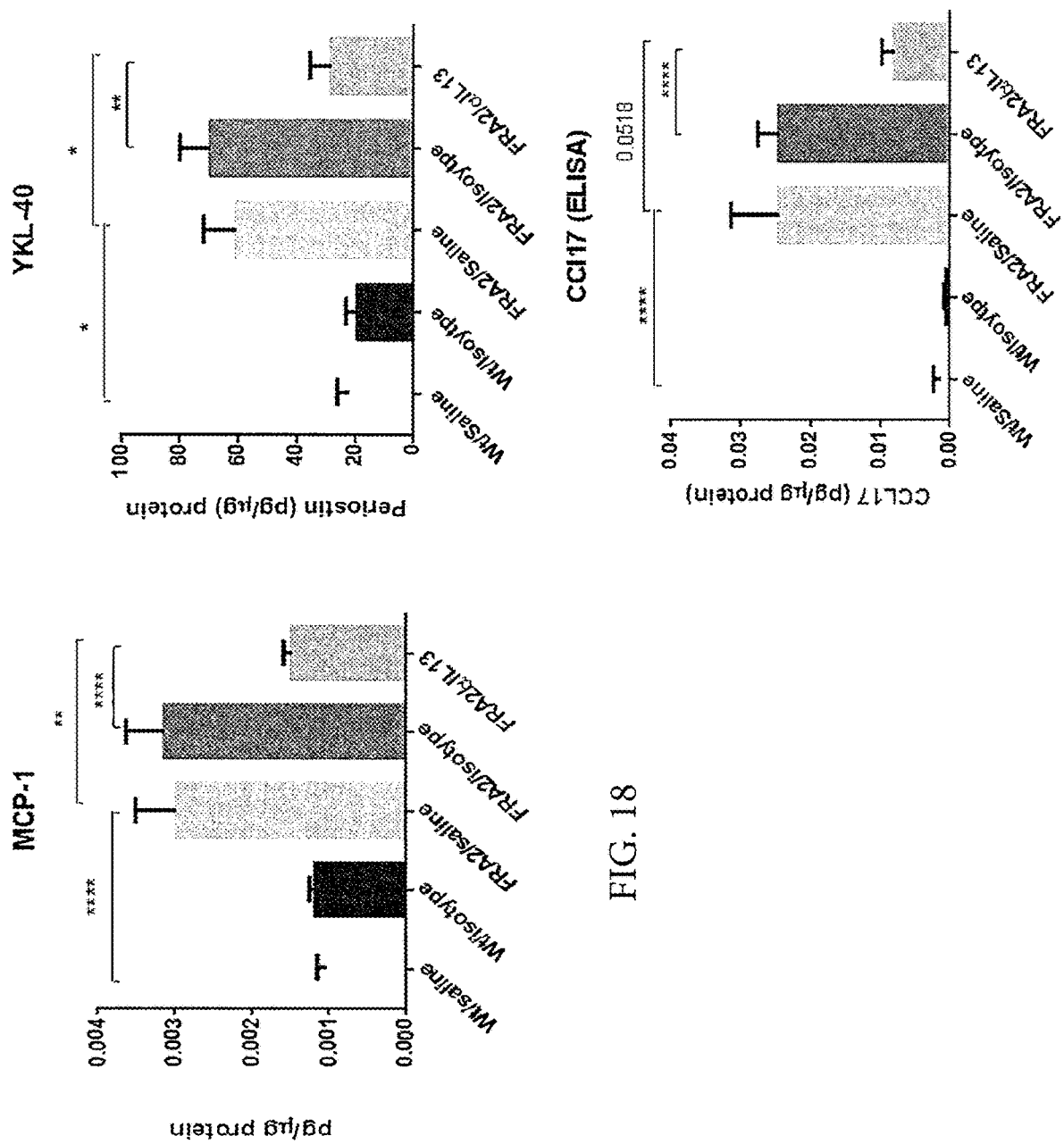
FIG. 18 shows MCP-1 (CCL2), CCL17, and YKL-40 protein expression levels in lung homogenates, as analyzed by ELISA.

MCP-1(CCL2) is a well characterized chemokine associated with pulmonary fibrosis and is regulated by IL-13. Similarly, CCL17/TARC and YKL-40 are IL-13 regulated proteins. Following the surrogate Ab treatment, CCL2, CCL17 and YKL-40 were significantly inhibited (FIG. 18).

Overall, these results demonstrate a role for IL-13 in promoting pulmonary fibrosis in the FRA2 mouse model. Inhibition of IL-13 expression is associated with a decrease in lung collagen content and pulmonary fibrosis related biomarkers.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

The invention claimed is:

1. A method of determining whether a dose comprising a dual-V-region bispecific antibody or a fragment thereof administered to a human subject specifically binds to IL-4 and IL-13 within the human subject, the method comprising:
   (a) administering the dose to the human subject;
   (b) measuring the amount of TARC/CCL17 protein in a blood, plasma, or serum sample drawn from the human subject, wherein a decrease in the amount of TARC/CCL17 in the blood sample relative to an amount of TARC/CCL17 in the subject measured before the dose was administered signifies binding of the dual-V-region bispecific antibody protein or fragment thereof to IL-4 or IL-13; and
   (c) increasing the dose if the decrease in TARC/CCL17 measured in step (b) is below a threshold value or decreasing the dose if the decrease in TARC/CCL17 measured in step (b) is above a threshold value, wherein the threshold value is a 20% to 60% decrease in the amount of TARC/CCL17 relative to the amount of TARC/CCL17 in the subject measured before the dose was administered;

wherein said dual-V-region bispecific antibody comprises a variable light chain domain and a variable heavy chain domain, wherein said variable light chain domain comprises amino acid sequences SEQ ID NO: 1 and SEQ ID NO: 3, wherein said variable heavy chain domain comprises amino acid sequences SEQ ID NO: 2 and SEQ ID NO: 4; and wherein the human subject has an IL-4 and/or IL-13 mediated disease.

2. The method of claim 1, wherein the threshold value is a 43% decrease in the amount of TARC/CCL17 relative to the amount of TARC/CCL17 in the subject measured before the dose was administered.

3. The method of claim 1, wherein the dose is administered subcutaneously.

4. The method of claim 1, wherein the amount of TARC/CCL17 is detected by enzyme-linked immunosorbent assay (ELISA).

5. The method of claim 1, wherein the human subject has idiopathic pulmonary fibrosis (IPF).

6. The method of claim 1, wherein the threshold value is a 40% to 50% decrease in the amount of TARC/CCL17 relative to the amount of TARC/CCL17 in the subject measured before the dose was administered.

* * * * *